(12) United States Patent
Shapiro et al.

(10) Patent No.: US 7,319,945 B1
(45) Date of Patent: Jan. 15, 2008

(54) AUTOMATED METHODS FOR SIMULATING A BIOLOGICAL NETWORK

(75) Inventors: Bruce E. Shapiro, Northridge, CA (US); Eric D. Mjolsness, Montrose, CA (US); Andre Levchenko, Columbia, MD (US)

(73) Assignee: California Institute of Technology, Pasadena, CA (US)

( * ) Notice: Subject to any disclaimer, the term of this patent is extended or adjusted under 35 U.S.C. 154(b) by 665 days.

(21) Appl. No.: 09/993,291

(22) Filed: Nov. 13, 2001

Related U.S. Application Data

(60) Provisional application No. 60/247,174, filed on Nov. 10, 2000.

(51) Int. Cl.
*G06F 9/455* (2006.01)

(52) U.S. Cl. .................. 703/11; 703/2; 435/6; 707/100

(58) Field of Classification Search ............. 703/2, 703/11; 435/6; 707/100; 706/50, 19, 46, 706/10; 702/19, 27; 600/436; 382/128; 514/46

See application file for complete search history.

(56) References Cited

U.S. PATENT DOCUMENTS

| | | | | |
|---|---|---|---|---|
| 5,808,918 | A * | 9/1998 | Fink et al. .................... | 703/11 |
| 5,914,891 | A * | 6/1999 | McAdams et al. ............ | 703/11 |
| 5,980,096 | A * | 11/1999 | Thalhammer-Reyero .... | 707/100 |
| 6,132,969 | A * | 10/2000 | Stoughton et al. ............. | 435/6 |
| 6,139,833 | A * | 10/2000 | Burgess et al. ............ | 424/93.2 |
| 6,173,276 | B1 * | 1/2001 | Kant et al. .................... | 706/50 |
| 6,175,761 | B1 * | 1/2001 | Frandsen et al. ........... | 600/436 |
| 6,219,440 | B1 * | 4/2001 | Schaff et al. ................ | 382/128 |
| 6,381,562 | B2 * | 4/2002 | Keane .......................... | 703/11 |
| 6,434,490 | B1 * | 8/2002 | Agrafiotis et al. ............ | 702/27 |
| 6,446,055 | B1 * | 9/2002 | Grand ......................... | 706/10 |
| 6,480,814 | B1 * | 11/2002 | Levitan ......................... | 703/2 |
| 6,490,573 | B1 * | 12/2002 | Njemanze .................... | 706/19 |
| 6,596,701 | B1 * | 7/2003 | Schwartz et al. ............. | 514/46 |
| 6,633,837 | B1 * | 10/2003 | Dye et al. ....................... | 703/9 |
| 6,708,141 | B1 * | 3/2004 | Schaff et al. .................. | 703/2 |
| 6,904,423 | B1 * | 6/2005 | Nicolaou et al. ............. | 706/46 |
| 6,983,227 | B1 * | 1/2006 | Thalhammer-Reyero ....... | 703/2 |

(Continued)

OTHER PUBLICATIONS

Fleischer et al., "Cellular texture generation", ACM 1995.*

(Continued)

*Primary Examiner*—K. Thangavelu
(74) *Attorney, Agent, or Firm*—DLA Piper US LLP

(57) ABSTRACT

The present invention relates to methods, computer systems, and computer programs for simulating a biological network. The methods of the present invention facilitate biological network simulations via automated equation generation based on the concept of a hierarchy of canonical forms that describe biological processes at various levels of detail. At each level of hierarchy two classes of canonical forms can be identified: the input canonical form, that is used to supply information to the program, and the output canonical form that is produced by a simulator. The methods in certain preferred embodiments include explicit output description and flexible user intervention at several steps through the model generation. Furthermore, preferred embodiments of the present invention provide the modeling of developmental networks using an organism-as-a-graph approach using domains and fields.

10 Claims, 29 Drawing Sheets

U.S. PATENT DOCUMENTS

| | | | |
|---|---|---|---|
| 2002/0002447 A1* | 1/2002 | Keane | 703/11 |
| 2002/0035459 A1* | 3/2002 | Grass et al. | 703/11 |
| 2002/0049542 A1* | 4/2002 | Rzhetsky et al. | 702/19 |

OTHER PUBLICATIONS

Bhalla and Iyengar, "Emergent Properties of Networks of Biological Signaling Pathways," *Science*, vol. 283, Jan. 15, 1999, pp. 381-387.

Ichikawa, Kazuhisa, "A-Cell: Graphical User Interface for the Construction of Biochemical Reaction Models," *Bioinformatics Applications Note*, vol. 17, No. 5, pp. 483-484, (2001).

Karp, Peter D., "MetaCyc: Metabolic Encyclopedia," Retrieved Nov. 11, 2001 from Eco/Cyc/MetaCyc Home Page Web site: http://malibu.ai.sri.com/ecocyc/.

Kohn, Kurt W., "Molecular Interaction Map of the Mammalian Cell Cycle Control and DNA Repair Systems," *Molecular Biology of the Cell*, vol. 10, Aug. 1999, pp. 2703-2734.

Levchenko, Andre et al., "Scaffold Proteins May Biphasically Affect the Levels of Mitogen-Activated Protein Kinase Signaling and Reduce Its Threshold Properties," *PNAS*, vol. 97, No. 11, May 23, 2000, pp. 5818-5823 and 4 figures.

Reinitz and Sharp, "Mechanism of *Eve* Stripe Formation," *Mechanisms of Development*, vol. 49, 1995, pp. 133-158.

Shapiro and Mjolsness, "Developmental Simulations with Cellerator," *International Conference on Systems Biology*, Abstract, Nov. 2, 2001, p. 118 and Table of Contents pp. 1-15.

Shapiro and Mjolsness, "Developmental Simulations with Cellerator," *International Conference on Systems Biology*, Abstract, Nov. 5-7, 2001, pp. 1-10.

Shapiro, Bruce E. et al., "Automatic Model Generation for Signal Transduction with Applications to MAP-Kinase Pathways," Foundations of Systems Biology, preprint of a paper to be published in 2001, pp. 1-17.

\* cited by examiner

```
              PFKA
r ={{ATP ⇌ ADP, k1, km1, k2},
    {∅ → ATP, v1},
    {ADP → ∅, v2},
    {PFK + ADP² ⇌ PFKA, k3, km3}};
interpret[r]

{{ADP'[t]== -v2 ADP[t]+k2 ATP_PFKA[t]-
    k3 ADP[t]² PFK[t]+km3 PFKA[t],
  ATP'[t]== v1+km1 ATP_PFKA[t]-
    k1 ATP[t]PFKA[t],
  ATP_PFKA'[t]== -k2 ATP_PFKA[t]-
    km1 ATP_PFKA[t]+k1 ATP[t] PFKA[t],
  PFK'[t]== -k3 ADP[t]² PFK[t]+km3 PFKA[t],
  PFKA'[t]== k2 ATP_PFKA[t]+
    km1 ATP_PFKA[t]+k3 ADP[t]² PFK[t]-
    km3 PFKA[t]-k1 ATP[t] PFKA[t]},
  {ADP,ATP,ATP_PFKA,PFK,PFKA}}
```

FIG. 3

```
gms = interpret[{
    {∅ ⇌ C,vi,kd},
    {C ⇌ ∅,hill[vmax→vd,khalf→kd]},
       x
    {Comp[M] ↦ M,hill[vmax→V1,khalf→K1]},
    {M ↦ ∅,hill[vmax→V2,khalf→K2]},
    {Comp[X] ↦ X,hill[vmax→VM3 * M[t],khalf→K3]},
    {X ↦ ∅,hill[vmax→V4,khalf→K4]}
    }]/.{V1 → VM1 * C[t]/(Kc+C[t])};
Print[gms];
run[gms,timeSpan → 500,MaxSteps → 5000,
    initialConditions →{C[0] ==.1,X[0] ==.1},
    plotVariables → All.
    rules → {
       K1→0.001,K2→0.001,K3→100,K4→100,
       vi→0.025,Kc→0.3,kd→0.01,VM1→3,
       V2→1.5,VM3→1,V4→0.5,vd→0.25,Kd→0.02
       },
    checkConstants → False
]
```

$$\{\{C'[t] == vi - kd\, C[t] - \frac{vd\, C[t]X[t]}{kd+C[t]},$$

$$M'[t] == \frac{VM1\, C[t]\, (1-M[t])}{(Kc+C[t])\, (1+K1-M[t])} - \frac{V2\, M[t]}{K2+M[t]},$$

$$X'[t] == \frac{VM3\, M[t]\, (1-X[t])}{1+K3-X[t]} - \frac{V4\, X[t]}{K4+X[t]}\}, \{C,M,X\}\}$$

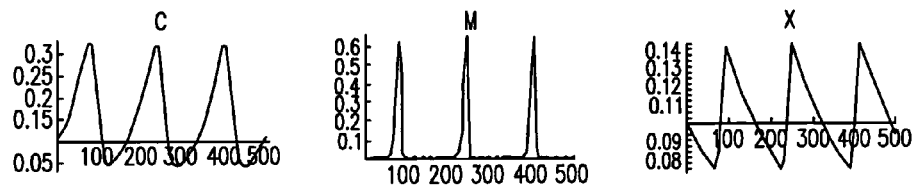

```
{{C→ InterpolatingFunction[{{0.,500.}},<>],
  M→ InterpolatingFunction[{{0.,500.}},<>],
  X→ InterpolatingFunction[{{0.,500.}},<>]}}
```

FIG. 8

```
g = unitGraph[odetype → local, threshold → 0.65,
    returnPointer → False];
TraditionalForm[g]
```

$\text{graphDomain}\Big(\text{nodes} \to \Big\{\text{nodeDomain}\big(\text{embedding} \to$ $\text{embeddingDomain}(\text{position} \to \{x(1), y(1), z(1)\}, \text{odes} \to \{x(1)'(t) == 0, y(1)'(t) == 0, z(1)'(t) == 0\},$
$\text{ic} \to \{x(1)(0) == 0.114318, y(1)(0) == 0.864451, z(1)(0) == 0.235455\}, \text{time} \to 0).$ $\text{models} \to \Big\{\text{modelDomain}\big(\text{molecules} \to \{c_1, M(1), X(1)\}, \text{odes} \to$ $\Big\{c'_1(t) == -\dfrac{0.25 X(1)(t) c_1[t]}{c_1[t]+0.01} - 0.01 c_1[t] + 0.025, M(1)'(t) == \dfrac{3 c_1[t](1-M(1)(t))}{c_1[t]+0.3}(1.005-M(1)(t)) -$ $\dfrac{1.5 M(1)(t)}{M(1)(t)+0.005}, X(1)'(t) == \dfrac{M(1)(t)(1-X(1)(t))}{1.005-X(1)(t)} - \dfrac{0.5 X(1)(t)}{X(1)(t)+0.005}\Big\},$ modelDomain(molecules →

$\text{ic} \to \{c_1[0] == 0.282391, M(1)(0) == 0, X(1)(0) == 0\}, \text{time} \to 0\Big), \text{modelDomain}(\text{molecules} \to$ $\{\text{splv}(1), \text{tspl}(1)\}, \text{odes} \to \{\text{splv}(1)'(t) == \theta(M(1)(t) - 0.65), \text{tspl}(1)'(t) == \theta(\text{splv}(1)(t) - 1. \times 10^{-8})\}.$
$\text{ic} \to \{\text{splv}(1)(0) == 0. \text{tspl}(1)(0) == 0\}, \text{time} \to 0\}, \text{modelDomain}(\text{molecules} \to \{\text{mass}(1)\},$
$\text{odes} \to \{\text{mass}(1)'(t) == \text{mu mass}(1)(t)\}, \text{ic} \to \{\text{mass}(1)(0) == 1\}, \text{time} \to 0)\Big\},$ $\text{nodeData} \to \{\text{birth} \to 0\}, \text{nodeType} \to \text{Cell}\Big)\Big\}, \text{links} \to \{\}, \text{lineage} \to \text{tree}(1)\Big)$

FIG. 9

```
genReacts [K,3,{2,2,1,1}, kpase]
    K[2,2]              K[2,2]                K[3,1]                K[3,1]              K[4,1]
{K[1,0] ⇌ K[1,1], K[1,1] ⇌ K[1,2], K[2,0] ⇌ K[2,1], K[2,1] ⇌ K[2,2], K[3,0] ⇌ K[3,1]}
        kpase[1]            kpase[1]            kpase[2]            kpase[2]            kpase[3]
```

FIG. 12

```
    RAFK
storeRateContant[db,RAF ⇌ RAF ★ ,a1,d1,k1,a2,d2,k2];
    RAFP
```

FIG. 13

```
phosphorylationReactions = genScafPhosReacts [S, {2,2,1,1},K,kpase]

{S[0,2,-1]→S[1,2,-1],S[0,2,0]→S[1,2,0],S[0,2,1]→S[1,2,1],S[1,2,-1]→S[2,2,-1],
S[1,2,0]→S[2,2,0],S[1,2,1]→S[2,2,1],S[-1,0,1]→S[-1,1,1],S[-1,1,1]→S[-1,2,1],
S[0,0,1]→S[0,1,1],S[0,1,1]→S[0,2,1],S[1,0,1]→S[1,1,1],S[1,1,1]→S[1,2,1],
                                              K[4,1]
S[2,0,1]→S[2,1,1],S[2,1,1]→S[2,2,1],S[-1,-1,0]⇌S[-1,-1,1],
                                              kpase[3]
           K[4,1]                      K[4,1]
S[-1,0,0]⇌S[-1,0,1],S[-1,1,0]⇌S[-1,1,1],S[-1,2,0]⇌S[-1,2,1],
           kpase[3]                    kpase[3]
           K[4,1]                      K[4,1]                      K[4,1]
S[0,-1,0]⇌S[0,-1,1],S[0,0,0]⇌S[0,0,1],S[0,1,0]⇌S[0,1,1],S[0,2,0]⇌S[0,2,1],
           kpase[3]                    kpase[3]                    kpase[3]
           K[4,1]                      K[4,1]                      K[4,1]
S[1,-1,0]⇌S[1,-1,1],S[1,0,0]⇌S[1,0,1],S[1,1,0]⇌S[1,1,1],S[1,2,0]⇌S[1,2,1],
           kpase[3]                    kpase[3]                    kpase[3]
           K[4,1]                      K[4,1]                      K[4,1]
S[2,-1,0]⇌S[2,-1,1],S[2,0,0]⇌S[2,0,1],S[2,1,0]⇌S[2,1,1],S[2,2,0]⇌S[2,2,1]}
           kpase[3]                    kpase[3]                    kpase[3]
```

FIG. 14

Receive initial condition values, process parameters, and a user representation of the biological network, wherein the user representation is input using one or more of a series of biological network canonical input forms, wherein each canonical input form is based on a type of biological process in the biological network. — 10

Generate a series of mathematical equations in an equation output canonical form based on the input representation of the biological network and the process parameters. — 20

Numerically solve the series of mathematical equations using the initial condition values and the process parameters, to generate a value or a table of values as a function of time for one or more output functions of the biological network, thereby simulating the biological network. — 40

FIG. 15

$$Out[2]=\begin{array}{l}\phantom{\{\{}\text{RAFK}\\\{\{K[3,0]\rightleftharpoons K[3,1],a1,d1,k1,a2,d2,k2\},\\\phantom{\{\{}\text{RAFP}\\\phantom{\{\{}K[3,1]\\\{K[2,0]\rightleftharpoons K[2,1],a3,d3,k3,a4,d4,k4\},\\\phantom{\{\{}\text{MEKP}\\\phantom{\{\{}K[3,1]\\\{K[2,1]\rightleftharpoons K[2,2],a5,d5,k5,a6,d6,k6\},\\\phantom{\{\{}\text{MEKP}\\\phantom{\{\{}K[2,2]\\\{K[1,0]\rightleftharpoons K[1,1],a7,d7,k7,a8,d8,k8\},\\\phantom{\{\{}\text{MAPKP}\\\phantom{\{\{}K[2,2]\\\{K[1,1]\rightleftharpoons K[1,2],a9,d9,k9,a10,d10,k10\}\\\phantom{\{\{}\text{MAPKP}\end{array}$$

FIG. 17
(Page 1 of 4)

```
{K[1,0] + S[-1,-1,-1] ⇌ S[0,-1,-1],kon,koff},
{K[1,0] + S[-1,-1,0] ⇌ S[0,-1,0],kon,koff},
{K[1,0] + S[-1,-1,1] ⇌ S[0,-1,1],kon,koff},
{K[1,0] + S[-1,0,-1] ⇌ S[0,0,-1],kon,koff},
{K[1,0] + S[-1,-0,0] ⇌ S[0,0,0],kon,koff},
{K[1,0] + S[-1,0,1] ⇌ S[0,0,1],kon,koff},
{K[1,0] + S[-1,1,-1] ⇌ S[0,1,-1],kon,koff},
{K[1,0] + S[-1,0,1] ⇌ S[0,1,0],kon,koff},
{K[1,0] + S[-1,1,1] ⇌ S[0,1,1],kon,koff},
{K[1,0] + S[-1,2,-1] ⇌ S[0,2,-1],kon,koff},
{K[1,0] + S[-1,2,0] ⇌ S[0,2,0],kon,koff},
{K[1,0] + S[-1,2,1] ⇌ S[0,2,1],kon,koff},
{K[1,1] + S[-1,-1,-1] ⇌ S[1,-1,-1],kpon,kpoff},
{K[1,1] + S[-1,-1,0] ⇌ S[1,-1,0],kpon,kpoff},
{K[1,1] + S[-1,-1,1] ⇌ S[1,-1,1],kpon,kpoff},
{K[1,1] + S[-1,0,-1] ⇌ S[1,0,-1],kpon,kpoff},
{K[1,1] + S[-1,0,0] ⇌ S[1,0,0],kpon,kpoff},
{K[1,1] + S[-1,0,1] ⇌ S[1,0,1],kpon,kpoff},
{K[1,1] + S[-1,1,-1] ⇌ S[1,1,-1],kpon,kpoff},
{K[1,1] + S[-1,1,0] ⇌ S[1,1,0],kpon,kpoff},
{K[1,1] + S[-1,1,1] ⇌ S[1,1,1],kpon,kpoff},
{K[1,1] + S[-1,2,-1] ⇌ S[1,2,-1],kpon,kpoff},
{K[1,1] + S[-1,2,0] ⇌ S[1,2,0],kpon,kpoff},
{K[1,1] + S[-1,2,1] ⇌ S[1,2,1],kpon,kpoff},
{K[1,2] + S[-1,-1,-1] ⇌ S[2,-1,-1],kpon,kpoff},
{K[1,2] + S[-1,-1,0] ⇌ S[2,-1,0],kpon,kpoff},
{K[1,2] + S[-1,-1,1] ⇌ S[2,-1,1],kpon,kpoff},
{K[1,2] + S[-1,0,-1] ⇌ S[2,0,-1],kpon,kpoff},
{K[1,2] + S[-1,0,0] ⇌ S[2,0,0],kpon,kpoff},
{K[1,2] + S[-1,0,1] ⇌ S[2,0,1],kpon,kpoff},
{K[1,2] + S[-1,1,-1] ⇌ S[2,1,-1],kpon,kpoff},
{K[1,2] + S[-1,1,0] ⇌ S[2,1,0],kpon,kpoff},
{K[1,2] + S[-1,1,-1] ⇌ S[2,1,1],kpon,kpoff},
{K[1,2] + S[-1,2,-1] ⇌ S[2,2,-1],kpon,kpoff},
{K[1,2] + S[-1,2,0] ⇌ S[2,2,0],kpon,kpoff},
{K[1,2] + S[-1,2,1] ⇌ S[2,2,1],kpon,kpoff},
{K[2,0] + S[-1,-1,-1] ⇌ S[-1,0,-1],kpon,kpoff},
{K[2,0] + S[-1,-1,0] ⇌ S[-1,0,0],kpon,kpoff},
{K[2,0] + S[-1,-1,1] ⇌ S[-1,0,1],kpon,kpoff},
{K[2,1] + S[-1,-1,-1] ⇌ S[-1,1,-1],kpon,kpoff},
{K[2,1] + S[-1,-1,0] ⇌ S[-1,1,0],kpon,kpoff},
{K[2,1] + S[-1,-1,1] ⇌ S[-1,1,1],kpon,kpoff},
{K[2,2] + S[-1,-1,-1] ⇌ S[-1,2,-1],kpon,kpoff},
{K[2,2] + S[-1,-1,0] ⇌ S[-1,2,0],kpon,kpoff},
{K[2,2] + S[-1,-1,1] ⇌ S[-1,2,1],kpon,kpoff},
{K[2,0] + S[0,-1,-1] ⇌ S[0,0,-1],kpon,kpoff},
{K[2,0] + S[0,-1,0] ⇌ S[0,0,0],kpon,kpoff},
{K[2,0] + S[0,-1,1] ⇌ S[0,0,1],kpon,kpoff},
{K[2,1] + S[0,-1,-1] ⇌ S[0,1,-1],kpon,kpoff},
{K[2,1] + S[0,-1,0] ⇌ S[0,1,0],kpon,kpoff},
{K[2,1] + S[0,-1,1] ⇌ S[0,1,1],kpon,kpoff},
{K[2,2] + S[0,-1,-1] ⇌ S[0,2,-1],kpon,kpoff},
```

FIG. 17
(Page 2 of 4)

```
{K[2,2] + S[0,-1,0] ⇌ S[0,2,0],kpon,kpoff},
{K[2,2] + S[0,-1,1] ⇌ S[0,2,1],kpon,kpoff},
{K[2,0] + S[1,-1,-1] ⇌ S[1,0,-1],kon,koff},
{K[2,0] + S[1,-1,0] ⇌ S[1,0,0],kon,koff},
{K[2,0] + S[1,-1,1]] ⇌ S[1,0,1],kon,koff},
{K[2,1] + S[1,-1,-1] ⇌ S[1,1,-1],kpon,kpoff},
{K[2,1] + S[1,-1,0] ⇌ S[1,1,0],kpon,kpoff},
{K[2,1] + S[1,-1,1] ⇌ S[1,-1,1],kpon,kpoff},
{K[2,2] + S[1,-1,-1] ⇌ S[1,2,-1],kpon,kpoff},
{K[2,2] + S[1,-1,0] ⇌ S[1,2,0],kpon,kpoff},
{K[2,2] + S[1,-1,-1] ⇌ S[1,2,1],kpon,kpoff},
{K[2,0] + S[2,-1,-1] ⇌ S[2,0,-1],kon,koff},
{K[2,0] + S[2,-1,0] ⇌ S[2,0,0],kon,koff},
{K[2,0] + S[2,-1,1] ⇌ S[2,0,1],kon,koff},
{K[2,1] + S[2,-1,1] ⇌ S[2,1,-1],kpon,kpoff},
{K[2,1] + S[2,-1,0] ⇌ S[2,1,0],kpon,kpoff},
{K[2,1] + S[2,-1,1] ⇌ S[2,1,1],kpon,kpoff},
{K[2,2] + S[2,-1,-1] ⇌ S[2,2,-1],kpon,kpoff},
{K[2,2] + S[2,-1,0] ⇌ S[2,2,0],kpon,kpoff},
{K[2,2] + S[2,-1,1] ⇌ S[2,2,1],kpon,kpoff},
{K[3,0] + S[-1,-1,-1] ⇌ S[1,-1,0],kon,koff},
{K[3,1] + S[-1,-1,-1] ⇌ S[-1,-1,1],kpon,kpoff},
{K[3,0] + S[-1,0,-1] ⇌ S[-1,0,0],kon,koff},
{K[3,1] + S[-1,0,-1] ⇌ S[-1,0,1],kpon,kpoff},
{K[3,0] + S[-1,1,-1] ⇌ S[-1,1,0],kon,koff},
{K[3,1] + S[-1,1,-1] ⇌ S[-1,1,1],kpon,kpoff},
{K[3,0] + S[-1,2,-1] ⇌ S[-1,2,0],kon,koff},
{K[3,1] + S[-1,2,-1] ⇌ S[-1,2,1],kpon,kpoff},
{K[3,0] + S[0,-1,-1] ⇌ S[0,-1,0],kon,koff},
{K[3,1] + S[0,-1,-1] ⇌ S[0,-1,1],kpon,kpoff},
{K[3,0] + S[0,0,-1] ⇌ S[0,0,0],kon,koff},
{K[3,1] + S[0,0,-1] ⇌ S[0,0,1],kpon,kpoff},
{K[3,0] + S[0,1,-1] ⇌ S[0,1,0],kon,koff},
{K[3,1] + S[0,1,-1] ⇌ S[0,1,1],kpon,kpoff},
{K[3,0] + S[0,2,-1] ⇌ S[0,2,0],kon,koff},
{K[3,1] + S[0,2,-1] ⇌ S[0,2,1],kpon,kpoff},
{K[3,0] + S[1,-1,-1] ⇌ S[1,-1,0],kon,koff},
{K[3,1] + S[1,-1,-1] ⇌ S[1,-1,1],kpon,kpoff},
{K[3,0] + S[1,0,-1] ⇌ S[1,0,0],kon,koff},
{K[3,1] + S[1,0,-1] ⇌ S[1,0,1],kpon,kpoff},
{K[3,0] + S[1,1,0-1] ⇌ S[1,1,0],kon,koff},
{K[3,1] + S[1,1,-1] ⇌ S[1,1,1],kpon,kpoff},
{K[3,0] + S[1,2,-1] ⇌ S[1,2,0],kon,koff},
{K[3,1] + S[1,2,-1] ⇌ S[1,2,1],kpon,kpoff},
{K[3,0] + S[2,-1,-1] ⇌ S[2,-1,0],kon,koff},
{K[3,1] + S[2,-1,-1] ⇌ S[2,-1,11],kpon,koff},
{K[3,0] + S[2,0,-1] ⇌ S[2,0,0],kon,koff},
{K[3,1] + S[2,0,-1] ⇌ S[2,0,1],kpon,kpoff},
{K[3,0] + S[2,1,-1] ⇌ S[2,1,0],kon,koff},
{K[3,1] + S[2,1,-1] ⇌ S[2,1,1],kpon,kpoff},
{K[3,0] + S[2,2,-1] ⇌ S[2,2,0],kon,koff},
{K[3,1] + S[2,2,-1] ⇌ S[2,2,1],kpon,kpoff},
```

FIG. 17
(Page 3 of 4)

{S[0,2,-1] → S[1,2,-1],k7},{S[0,2,0] → S[1,2,0],k7},
{S[0,2,1] → S[1,2,1],k7},{S[1,2,-1] → S[2,2,-1],k9a},
{S[1,2,0] → S[2,2,0],k9a},{S[1,2,1] → S[2,2,1],k9a},
{S[-1,0,1] → S[-1,1,1],k3},{S[-1,1,1] → S[-1,2,1],k5a},
{S[0,0,1] → S[0,1,1],k3},{S[0,1,1] → S[0,2,1],k5a},
{S[1,0,1] → S[1,1,1],k3},{S[1,1,1] → S[1,2,1],k5a},
{S[2,0,1] → S[2,1,1],k3},{S[2,1,1] → S[2,2,1],k5a},
{S[1,1,0] $\underset{}{\overset{RAFK}{\rightleftarrows}}$ S[-1,-1,1],k1a,d1a,k1}, {S[-1,0,0] $\underset{}{\overset{RAFK}{\rightleftarrows}}$ S[-1,0,1],k1a,d1a,k1}, {S[-1,1,0] $\underset{}{\overset{RAFK}{\rightleftarrows}}$ S[-1,1,1],k1a,d1a,k1}, {S[-1,2,0] $\underset{}{\overset{RAFK}{\rightleftarrows}}$ S[-1,2,1],k1a,d1a,k1}, {S[0,-1,0] $\underset{}{\overset{RAFK}{\rightleftarrows}}$ S[0,-1,1],k1a,d1a,k1}, {S[0,0,0] $\underset{}{\overset{RAFK}{\rightleftarrows}}$ S[0,0,1],k1a,d1a,k1}, {S[0,1,0] $\underset{}{\overset{RAFK}{\rightleftarrows}}$ S[0,1,1],k1a,d1a,k1}, {S[0,2,0] $\underset{}{\overset{RAFK}{\rightleftarrows}}$ S[0,2,1],k1a,d1a,k1}, {S[1,-1,0] $\underset{}{\overset{RAFK}{\rightleftarrows}}$ S[1,-1,1],k1a,d1a,k1}, {S[1,0,0] $\underset{}{\overset{RAFK}{\rightleftarrows}}$ S[1,0,1],k1a,d1a,k1}, {S[1,1,0] $\underset{}{\overset{RAFK}{\rightleftarrows}}$ S[1,1,1],k1a,d1a,k1}, {S[1,2,0] $\underset{}{\overset{RAFK}{\rightleftarrows}}$ S[1,2,1],k1a,d1a,k1}, {S[2,1,0] $\underset{}{\overset{RAFK}{\rightleftarrows}}$ S[2,-1,1],k1a,d1a,k1}, {S[2,0,0] $\underset{}{\overset{RAFK}{\rightleftarrows}}$ S[2,0,1],k1a,d1a,k1}, {S[2,1,0] $\underset{}{\overset{RAFK}{\rightleftarrows}}$ S[2,1,1],k1a,d1a,k1}, {S[2,2,0] $\underset{}{\overset{RAFK}{\rightleftarrows}}$ S[2,2,1],k1a,d1a,k1},

FIG. 17
(Page 4 of 4)

Out[3]= {{MAPKP'[t]== -a8 MAPKP[t] K[1,1][t]
    a10 MAPKP[t] K[1,2][t]+d8 K#MAPKP[1,1][t]+k8 K#MAPKP[1,1][t]
    d10 D#MAPKP[1,2][t]+k10 K#MAPKP[1,2],MEKP[t]==
    a4 MEKP[t]K[2,1][t]+a6 MEKP[t]K[2,2][t]+d4 K#MEKP[2,1][t]+
    k4 K#MEKP[2,1][t]+d6 K#MEKP[2,2][t]+k6 K#MEKP[2,2][t],
RAFK[t]== -a1 RAFK[t] K[3,0][t]+d1 K#RAFK[3,0][t],
    k1 K#RAFK[3,0][t]+k1a RAFK[t] S[-1,-1,0][t]

FIG. 18
(Page 1 of 10)

```
k1a RAFK[t] S[-1,0,0][t] - k1a RAFK[t] S[-1,1,0][t]-
k1a RAFK[t] S[-1,2,0][t] - k1a RAFK[t] S[0,-1,0][t]-
k1a RAFK[t] S[0,0,0][t] - k1a RAFK[t] S[0,1,0][t]-
k1a RAFK[t] S[0,2,0][t] - k1a RAFK[t] S[1,-1,0][t]-
k1a RAFK[t] S[1,0,0][t] - k1a RAFK[t] S[1,1,0][t]-
k1a RAFK[t] S[1,2,0][t] - k1a RAFK[t] S[2,-1,0][t]-
k1a RAFK[t] S[2,0,0][t] - k1a RAFK[t] S[2,1,0][t]-
k1a RAFK[t] S[2,2,0][t] + d1a S#RAFK[-1,-1,0][t]+
k1 S#RAFK[-1,-1,0][t] + d1a S#RAFK[-1,0,0][t]+
k1 S#RAFK[-1,0,0][t] + d1a S#RAFK[-1,1,0][t]+
k1 S#RAFK[-1,1,0][t] + d1a S#RAFK[-1,2,0][t]+
k1 S#RAFK[-1,2,0][t] + d1a S#RAFK[0,-1,0][t]+
k1 S#RAFK[0,-1,0][t] + d1a S#RAFK[0,0,0][t]+
k1 S#RAFK[0,0,0][t] + d1a S#RAFK[0,1,0][t]+
k1 S#RAFK[0,1,0][t] + d1a S#RAFK[0,2,0][t]+
k1 S#RAFK[0,2,0][t] + d1a S#RAFK[1,-1,0][t]+
k1 S#RAFK[1,-1,0][t] + d1a S#RAFK[1,0,0][t]+
k1 S#RAFK[1,0,0][t] + d1a S#RAFK[1,1,0][t]+
k1 S#RAFK[1,1,0][t] + d1a S#RAFK[1,2,0][t]+
k1 S#RAFK[1,2,0][t] + d1a S#RAFK[2,-1,0][t]+
k1 S#RAFK[2,-1,0][t] + d1a S#RAFK[2,0,0][t]+
k1 S#RAFK[2,0,0][t] + d1a S#RAFK[2,1,0][t]+
k1 S#RAFK[2,1,0][t] + d1a S#RAFK[2,2,0][t] + k1 S#RAFK[2,2,0][t],
RAFP[t]==-a2 RAFP[t] K[3,1][t] - d2 K#RAFP[3,1][t] +
  k2 K#RAFP[3,1][t],K[1,0]'[t]==
a7 K[1,0][t] K[2,2][t] + d7 K#K[1,0,2,2][t] + k8 K#MAPKP[1,1][t] -
kon K[1,0][t] S[-1,-1,-1][t] - kon K[1,0][t] S[-1,-1,0][t] -
kon K[1,0][t] S[-1,-1,1][t] - kon K[1,0][t] S[-1,0,-1][t] -
kon K[1,0][t] S[-1,0,0][t] - kon K[1,0][t] S[-1,0,1][t] -
kon K[1,0][t] S[-1,1,-1][t] - kon K[1,0][t] S[-1,1,0][t] -
kon K[1,0][t] S[-1,1,1][t] - kon K[1,0][t] S[-1,2,-1][t] -
kon K[1,0][t] S[-1,2,0][t] - kon K[1,0][t] S[-1,2,1][t] -
koff S[0,-1,-1][t] + koff S[0,-1,0][t] + koff S[0,-1,1][t] +
koff S[0,0,-1][t] + koff S[0,0,0][t] + koff S[0,0,1][t] +
koff S[0,1,-1][t] + koff S[0,1,0][t] + koff S[0,1,1][t] +
koff S[0,2,-1][t] + koff S[0,2,0][t] + koff S[0,2,1][t] +
K[1,1][t]==-a8 MAPKP[t] K[1,1][t] - a9 K[1,1][t] K[2,2][t] +
  k7 K#K[1,0,2,2][t] + d9 K#K[1,1,2,2][t] + d8 K#MAPKP[1,1][t] +
  k10 K#MAPKP[1,2][t] - kpon K[1,1][t] S[-1,-1,-1][t] -
kpon K[1,1][t] S[-1,-1,0][t] - kpon K[1,1][t] S[-1,-1,1][t] -
kpon K[1,1][t] S[-1,0,-1][t] - kpon K[1,1][t] S[-1,0,0][t] -
kpon K[1,1][t] S[-1,0,1][t] - kpon K[1,1][t] S[-1,1,-1][t] -
kpon K[1,1][t] S[-1,1,0][t] - kpon K[1,1][t] S[-1,1,1][t] -
kpon K[1,1][t] S[-1,2,-1][t] - kpon K[1,1][t] S[-1,2,0][t] -
kpon K[1,1][t] S[-1,2,1][t] + kpoff S[1,-1,-1][t] +
kpoff S[1,-1,0][t] + kpoff S[1,-1,1][t] +
kpoff S[1,0,-1][t] + kpoff S[1,0,0][t] + kpoff S[1,0,1][t] +
kpoff S[1,1,-1][t] + kpoff S[1,1,0][t] + kpoff S[1,1,1][t] +
kpoff S[1,2,-1][t] + kpoff S[1,2,0][t] + kpoff S[1,2,1][t],
K[1,2]'[t]==-a10 MAPKP[t] K[1,2][t] + k9 K#K[1,1,2,2][t] +
  d10 K#MAPKP[1,2][t] - kpon K[1,2][t] S[-1,-1,-1][t] -
kpon K[1,2][t] S[-1,-1,0][t] - kpon K[1,2][t] S[-1,-1,1][t] -
```

FIG. 18

(Page 2 of 10)

```
    kpon K[1,2][t] S[-1,0,-1][t] - kpon K[1,2][t] S[-1,0,0][t] -
    kpon K[1,2][t] S[-1,0,1][t] - kpon K[1,2][t] S[-1,1,-1][t] -
    kpon K[1,2][t] S[-1,1,0][t] - kpon K[1,2][t] S[-1,1,1][t] -
    kpon K[1,2][t] S[-1,2,-1][t] - kpon K[1,2][t] S[-1,2,0][t] -
    kpon K[1,2][t] S[-1,2,1][t] - kpoff S[2,-1,-1][t] +
    kpoff S[2,-1,0][t] + kpoff S[2,-1,1][t] +
    kpoff S[2,0,-1][t] + kpoff S[2,0,0][t] + kpoff S[2,0,1][t] +
    kpoff S[2,1,-1][t] + kpoff S[2,1,0][t] + kpoff S[2,1,1][t] +
    kpoff S[2,2,-1][t] + kpoff S[2,2,0][t] + kpoff S[2,2,1][t],
K[2,0]'[t]==-a3 K[2,0][t] K[3,1][t] + d3 K#K[2,0,3,1][t] +
    k4 K#MEKP[2,1][t] - kon K[2,0][t] S[-1,-1,-1][t] -
    kon K[2,0][t] S[-1,-1,0][t] - kon K[2,0][t] S[-1,-1,1][t] +
    koff S[-1,0,-1][t] + koff S[-1,0,0][t] +
    koff S[-1,0,1][t] + kon K[2,0][t] S[0,-1,-1][t] -
    kon K[2,0][t] S[0,-1,0][t] - kon K[2,0][t] S[0,-1,1][t] +
    koff S[0,0,-1][t] + koff S[0,0,0][t] +
    koff S[0,0,1][t] - kon K[2,0][t] S[1,-1,-1][t] -
    kon K[2,0][t] S[1,-1,0][t] - kon K[2,0][t] S[1,-1,1][t] +
    koff S[1,0,-1][t] + koff S[1,0,0][t] +
    koff S[1,0,1][t] - kon K[2,0][t] S[2,-1,-1] [t] -
    kon K[2,0] [t] S[2,-1,0][t] - kon K[2,0][t] S[2,-1,1][t] +
    koff S[2,0,-1][t] + koff S[2,0,0][t] + koff S[2,0,1][t],
K[2,1]'[t]==-a4 MEKP[t] K[2,1][t] - a5 K[2,1][t] K[3,1][t] +
    k3 K#K[2,3,-1][t] + d5 K#K[2,1,3,1][t] + d4 K#MEKP[2,1][t] +
    k6 K#MEKP[2,2][t], kpon K[2,1][t] S[-1,-1,-1][t] -
    kpon K[2,1][t] S[-1,-1,0][t] - kpon K[2,1][t] S[-1,-1,1][t] +
    kpoff S[-1,1,-1][t] + kpoff S[-1,1,0][t] +
    kpoff S[-1,1,1][t] - kpon K[2,1][t] S[0,-1,-1][t] -
    kpon K[2,1][t] S[0,-1,0][t] - kpon K[2,1][t] S[0,-1,1][t] +
    kpoff S[0,1,-1][t] - kpoff S[0,1,0][t] +
    kpoff S[0,1,1][t] - kpon K[2,1][t] S[1,-1,-1][t] -
    kpon K[2,1][t] S[1,-1,0][t] - kpon K[2,1][t] S[1,-1,1][t] +
    kpoff S[1,1,-1][t] + kpoff S[1,1,0][t] +
    kpoff S[1,1,1][t] - kpon K[2,1][t] S[2,-1,-1][t] -
    kpon[2,1][t] S[2,-1,0][t] - kpon K[2,1][t] S[2,-1,1][t] +
    kpoff S[2,1,-1][t] + kpoff S[2,1,0][t] + kpoff S[2,1,1][t],
K[2,2]'[t]==-a6 MEKP[t] K[2,2][t] - a7 K[1,0][t] K[2,2][t] -
    a9 K[1,1][t] K[2,2][t] + d7 K#K[1,0,2,2][t] +
    k7 K#K[1,0,2,2][t] + d9 K#K[1,1,2,2][t] +
    k9 K#K[1,1,2,2][t] + k5 K#K[2,1,3,1][t] +
    d6 K#MEKP[2,2][t] - kpon K[2,2][t] S[-1,-1,-1][t] -
    kpon K[2,2][t] S[-1,-1,0][t] - kpon K[2,2][t] S[-1,-1,1][t] +
    kpoff S[-1,2,-1][t] - kpoff S[-1,2,0][t] +
    kpoff S[-1,2,1][t] - kpon K[2,2][t] S[0,-1,-1][t] -
    kpon K[2,2][t] S[0,-1,0][t] - kpon K[2,2][t] S[0,-1,1][t] +
    kpoff S[0,2,-1][t] + kpoff S[0,2,0][t] +
    kpoff S[0,2,-1][t] + kpon K[2,2][t] S[1,-1,-1][t] -
    kpon K[2,2][t] S[1,-1,0][t] - kpon K[2,2][t] S[1,-1,1][t] +
    kpoff S[1,2,-1][t] + kpoff S[1,2,0][t] +
    kpoff S[1,2,1][t] - kpon K[2,2][t] S[2,-1,-1][t] -
    kpon K[2,2][t] S[2,-1,0][t] - kpon K[2,2][t] S[2,-1,1][t] +
    kpoff S[2,2,-1][t] - kpoff S[2,2,0][t] + kpoff S[2,2,1][t],
```

FIG. 18
(Page 3 of 10)

```
K[3,0]'[t]==-a1 RAFK[t] K[3,0][t] + d1 K#RAFK[3,0][t] +
  k2 K#RAFP[3,1][t] - kon K[3,0][t] S[-1,-1,-1][t] +
  koff S[-1,-1,0][t] - kon K[3,0][t] S[-1,0,-1][t] +
  koff S[-1,0,0][t] - kon K[3,0][t] S[-1,1,-1][t] +
  koff S[-1,1,0][t] - kon K[3,0][t] S[-1,2,-1][t] +
  koff S[-1,2,0][t] - kon K[3,0][t] S[0,-1,-1][t] +
  koff S[0,-1,0][t] - kon K[3,0][t] S[0,0,-1][t] +
  koff S[0,0,0][t] - kon K[3,0][t] S[0,1,-1][t] +
  koff S[0,1,0][t] - kon K[3,0][t] S[0,2,-1][t] +
  koff S[0,2,0][t] - kon K[3,0][t] S[1,-1,-1][t] +
  koff S[1,-1,0][t] - kon K[3,0][t] S[1,0,-1][t] +
  koff S[1,0,0][t] - kon K[3,0][t] S[1,1,-1][t] +
  koff S[1,1,0][t] - kon K[3,0][t] S[1,2,-1][t] +
  koff S[1,2,0][t] - kon K[3,0][t] S[2,-1,-1][t] +
  koff S[2,-1,0][t] - kon K[3,0][t] S[2,0,-1][t] +
  koff S[2,0,0][t] - kon K[3,0][t] S[2,1,-1][t] +
  koff S[2,1,0][t] - kon K[3,0][t] S[2,2,-1][t] + koff S[2,2,0][t],
K[3,1]'[t]==-a2 RAFP[t] K[3,1][t] -a3 K[2,0][t] K[3,1][t] -
  a5 K[2,1][t] K[3,1][t] + d3 K#K[2,0,3,1][t] +
  k3 K#K[2,0,3,1][t] + d5 K#K[2,1,3,1][t] +
  k5 K#K[2,1,2,1][t] + k1 K#RAFK[3,0][t] + d2 K#RAFP[3,1][t] -
  kpon K[3,1][t] S[-1,-1,-1][t] + kpoff S[-1,-1,1][t] -
  kpon K[3,1][t] S[-1,0,-1][t] + kpoff S[-1,0,1][t] -
  kpon K[3,1][t] S[-1,1,-1][t] + kpoff S[-1,1,1][t] -
  kpon K[3,1][t] S[-1,2,-1][t] + kpoff S[-1,2,1][t] -
  kpon K[3,1][t] S[0,-1,-1][t] + kpoff S[0,-1,1][t] -
  kpon K[3,1][t] S[0,0-1][t] + kpoff S[0,0,1][t] -
  kpon K[3,1][t] S[0,1,-1][t] + kpoff S[0,1,1][t] -
  kpon K[3,1][t] S[0,2,-1][t] + kpoff S[0,2,1][t] -
  kpon K[3,1][t] S[1,-1,-1][t] + kpoff S[1,-1,1][t] -
  kpon K[3,1][t] S[1,0,-1][t] + kpoff S[1,0,1][t] -
  kpon K[3,1][t] S[1,1,-1][t] + kpoff S[1,1,1][t] -
  kpon K[3,1][t] S[1,2,-1][t] + kpoff S[1,2,1][t] -
  kpon K[3,1][t] S[2,-1,-1][t] + kpoff S[2,-1,1][t] -
  kpon K[3,1][t] S[2,0,-1][t] + kpoff S[2,0,1][t] -
  kpon K[3,1][t] S[2,1,-1][t] + kpoff S[2,1,1][t] -
  kpon K[3,1][t] S[2,2,-1][t] + kpoff S[2,2,1][t],
K#K[1,0,2,2][t]==-a7 K[1,0][t] K[2,2][t] -
  d7 K#K[1,0,2,2][t] - k7 K#K[1,0,2,2][t],
K#K[1,1,2,2][t]==-a9 K[1,1][t] K[2,2][t] -
  d9 K#K[1,1,2,2][t] - k9 K#K[1,1,2,2][t],
K#K[2,0,3,1][t]==-a3 K[2,0][t] K[3,1][t] -
  d3 K#K[2,0,3,1][t] - k3 K#K[2,0,3,1][t],
K#K[2,1,3,1][t]==-a5 K[2,1][t] K[3,1][t] - d5 K#K[2,1,3,1][t] -
  k5 K#K[2,1,3,1][t] - K#MAPKP[1,1]'[t]==
a8 MAPKP[t] K[1,-1][t] - d8 K#MAPKP[1,1][t] - k8 K#MAPKP[1,1][t],
K#MAPKP[1,2]'[t]==-a10 MAPKP[t] K[1,2][t] -
  d10 K#MAPKP[1,2][t] - k10 K#MAPKP[1,2][t],
K#MEKP[2,1]'[t]==-a4 MEKP[t] K[2,1][t] - d4 K#MEKP[2,1][t] -
  k4 K#MEKP[2,1][t], K#MEKP[2,2]'[t]==
a6 MEKP[t] K[2,2][t] - d6 K#MEKP[2,2][t] - k6 K#MEKP[2,2][t],
K#RAFK[3,0]'[t]==-a1 RAFK[t] K[3,0][t] - d1 K#RAFK[3,0][t] -
```

FIG. 18

```
k1 K#RAFK[3,0][t], K#RAFP[3,1]'[t]==
 a2 RAFP[t] K[3,1][t] - d2 K#RAFP[3,1][t] - k2 K#RAFP[3,1][t],
S[-1,-1,-1]'[t]==-kon K[1,0][t] S[-1,-1,-1][t] -
  kpon K[1,1][t] S[-1,-1,-1][t] - kpon K[1,2][t] S[-1,-1,-1][t] -
  kon K[2,0][t] S[-1,-1,-1][t] - kpon K[2,1][t] S[-1,-1,-1][t] -
  kpon K[2,2][t] S[-1,-1,-1][t] - kon K[3,0][t] S[-1,-1,-1][t] -
  kpon K[3,1][t] S[-1,-1,-1][t] + koff S[-1,-1,0][t] +
  kpoff S[-1,-1,1][t] + koff S[-1,0,-1][t] +
  kpoff S[-1,1,-1][t] + kpoff S[-1,2,-1][t] +
  koff S[0,-1,-1][t] - kpoff S[1,-1,-1][t] + kpoff S[2,-1,-1][t],
S[-1,-1,0]'[t]== kon K[3,0][t] S[-1,-1,-1][t] -
  koff S[-1,-1,0][t] - kla RAFK[t] S[-1,-1,0][t] -
  kon K[1,0][t] S[-1,-1,0][t] - kpon K[1,1][t] S[-1,-1,0][t] -
  kpon K[1,2][t] S[-1,-1,0][t] - kon K[2,0][t] S[-1,-1,0][t] -
  kpon K[2,1][t] S[-1,-1,0][t] + kpon K[-2,2][t] S[-1,-1,0][t] +
  kpoff S[-1,0,0][t] + kpoff S[-1,1,0][t] +
  kpoff S[-1,2,0][t] + koff S[0,-1,0][t] + kpoff S[1,-1,0][t] +
  kpoff S[2,-1,0][t] - dla S#RAFK[-1,-1,0][t],
S[-1,-1,1]'[t]== kpon K[3,1][t] S[-1,-1,-1][t] -
  kpoff S[-1,-1,0][t] - kon K[1,0][t] S[-1,-1,1][t] -
  kpon K[1,1][t] S[-1,-1,1][t] - kpon K[1,2][t] S[-1,-1,1][t] -
  kon K[2,0][t] S[-1,-1,1][t] - kpon K[2,1][t] S[-1,-1,1][t] -
  kpon K[2,2][t] S[-1,-1,1][t] + koff S[-1,0,1][t] +
  kpoff S[-1,1,1][t] + kpoff S[-1,2,1][t] + koff S[0,-1,1][t] +
  kpoff S[1,-1,1][t] + kpoff S[2,-1,1][t] + k1 S#RAFK[-1,-1,0][t],
S[-1,0,-1]'[t]= kon K[2,0][t] S[-1,-1,-1][t] -
  koff S[-1,0,-1][t] - kon K[1,0][t] S[-1,0,-1][t] -
  kpon K[1,1][t] S[-1,0,-1][t] - kpon K[1,2][t] S[-1,0,-1][t] -
  kon K[3,0][t] S[-1,0,-1][t] - kpon K[3,1][t] S[-1,0,-1][t] +
  koff S[-1,0,0][t] + kpoff S[-1,0,1][t] + koff S[0,0,-1][t] +
  kpoff S[1,0,-1][t] + kpoff S[2,0,-1][t] , S[-1,0,0][t] =
 kon K[2,0][t] S[-1,-1,0][t] + kon K[3,0][t] S[-1,0,-1][t] -
 2 koff S[-1,0,0][t] - kla RAFK[t] S[-1,0,0][t] -
 kon K[1,0][t] S[-1,0,0][t] - kpon K[1,1][t] S[-1,0,0][t] -
 kpon K[1,2][t] S[-1,0,0][t] + koff S[0,0,0][t] +
 kpoff S[1,0,0][t] + kpoff S[2,0,0][t] + dla S#RAFK[-1,0,0][t],
S[-1,0,1]'[t]== kon K[2,0][t] S[-1,-1,1][t] +
  kpon K[3,1][t] S[-1,0,-1][t] - k3 S[-1,0,1][t] -
  koff S[-1,0,1][t] - kpoff S[-1,0,1][t] -
  kon K[1,0][t] S[-1,0,1][t] - kpon K[1,1][t] S[-1,0,1][t] -
  kpon K[1,2][t] S[-1,0,1][t] + koff S[0,0,1][t] +
  kpoff S[1,0,1][t] + kpoff S[2,0,1][t] + k1 S#RAFK[-1,0,0][t],
S[-1,1,-1]'[t]== kpon K[2,1][t] S[-1,-1,-1][t] -
  kpoff S[-1,1,-1][t] - kon K[1,0][t] S[-1,1,-1][t] -
  kpon K[1,1][t] S[-1,1,-1][t] - kpon K[1,2][t] S[-1,1,-1][t] -
  kon K[3,0][t] S[-1,1,-1][t] - kpon K[3,1][t] S[-1,1,-1][t] +
  koff S[-1,1,0][t] + kpoff S[-1,1,1][t] + koff S[0,1,-1][t] +
  kpoff S[1,1,-1][t] + kpoff S[2,1,-1][t],
S[-1,1,0]'[t]= = kpon K[2,1][t] S[-1,-1,0][t] +
  kon K[3,0][t] S[-1,1,-1][t] - koff S[-1,1,0][t] -
  kpoff S[-1,1,0][t] - kla RAFK[t] S[-1,1,0][t] -
  kon K[1,0][t] S[-1,1,0][t] - kpon K[1,1][t] S[-1,1,0][t] -
```

FIG. 18

(Page 5 of 10)

```
  kpon K[1,2][t] S[-1,1,0][t] + koff S[0,1,0][t] +
  kpoff S[1,1,0,][t] + kpoff S[2,1,0][t] + dla S#RAFK[-1,1,0][t],
S[-1,1,1]'[t]==kpon K[2,1][t] S[-1,-1,1][t] +
  k3 S[-1,0,1][t] + kpon K[3,1][t] S[-1,1,-1][t] -
  k5a S[-1,1,1][t] - 2 kpoff S[-1,1,1][t] -
  kon K[1,0][t] S[-1,1,1][t] - kpon K[1,1][t] S[-1,1,1][t] -
  kpon K[1,2][t] S[-1,1,1][t] + koff S[0,1,1][t] +
  kpoff S[1,1,1][t] + kpoff S[2,1,1][t] + k1 S#RAFK[-1,1,0][t],
S[-1,2,-1]'[t]== kpon K[2,2][t] S[-1,-1,-1][t] -
  kpoff S[-1,2,-1][t] - kon K[1,0][t] S[-1,2,-1][t] -
  kpon K[1,1][t] S[-1,2,-1][t] - kpon K[1,2][t] S[-1,2,-1][t] -
  kon K[3,0][t] S[-1,2,-1][t] - kpon K[3,1][t] S[-1,2,-1][t] +
  koff S[-1,2,0][t] + kpoff S[-1,2,1][t] + koff S[0,2,-1][t] +
  kpoff S[1,2,-1][t] + kpoff S[2,2,-1][t],
S[-1,2,0]'[t]== kpon K[2,2][t] S[-1,-1,0][t] +
  kon K[3,0][t] S[-1,2,-1][t] - koff S[-1,2,0][t] -
  kpoff S[-1,2,0][t] - kla RAFK[t] S[-1,2,0][t] -
  kon K[1,0][t] S[-1,2,0][t] - kpon K[1,1][t] S[-1,2,0][t] -
  kpon K[1,2][t] S[-1,2,0][t] + koff S[0,2,0][t] +
  kpoff S[1,2,0][t] + kpoff S[2,2,0][t] + dla S#RAFK[-1,2,0][t],
S[-1,2,1]'[t]== kpon K[2,2][t] S[-1,-1,1][t] + k5a S[-1,1,1][t] +
  kpon K[3,1][t] S[-1,2,-1][t] - 2 kpoff S[-1,2,1][t] -
  kon K[1,0][t] S[-1,2,1][t] - kpon K[1,1][t] S[-1,2,1][t] -
  kpon K[1,2][t] S[-1,2,1][t] + koff S[0,2,1][t] +
  kpoff S[1,2,1][t] + kpoff S[2,2,1][t] + k1 S#RAFK[-1,2,0][t],
S[0,-1,-1]'[t]== kon K[1,0][t] S[-1,-1,-1][t] -
  koff S[0,-1,-1][t] - kon K[2,0][t] S[0,-1,-1][t] -
  kpon K[2,1][t] S[0,-1,-1][t] - kpon K[2,2][t] S[0,-1,-1][t] -
  kon K[3,0][t] S[0,-1,-1][t] + kpon K[3,1][t] S[0,-1,-1][t] +
  koff S[0,-1,0][t] + kpoff S[0,-1,1][t] + koff S[0,0,-1][t] +
  kpoff S[0,1,-1][t] + kpoff S[0,2,-1][t], S[0,-1,0]'[t]==
  kon K[1,0][t] S[-1,-1,0][t] + kon K[3,0][t] S[0,-1,-1][t] -
  2 koff S[0,-1,0][t] - kla RAFK[t] S[0,-1,0][t] -
  kon K[2,0][t] S[0,-1,0][t] - kpon K[2,1][t] S[0,-1,0][t] -
  kpon K[2,2][t] S[0,-1,0][t] + koff S[0,0,0][t] +
  kpoff S[0,1,0][t] + kpoff S[0,2,0][t] + dla S#RAFK[0,-1,0][t],
S[0,-1,1]'[t]== kon K[1,0][t] S[-1,-1,1][t] +
  kpon K[3,1][t] S[0,-1,-1][t] - koff S[0,-1,1][t] -
  kpoff S[0,-1,1][t] - kon K[2,0][t] S[0,-1,1][t] -
  kpon K[2,1][t] S[0,-1,1][t] - kpon K[2,2][t] S[0,-1,1][t] +
  koff S[0,0,1][t] + kpoff S[0,1,1][t] +
  kpoff S[0,2,1][t] + k1 S#RAFK[0,-1,0][t],
S[0,0,-1]'[t]== kon K[1,0][t] S[-1,0,-1][t] +
  kon K[2,0][t] S[0,-1,-1][t] - 2 koff S[0,0,-1][t] -
  kon K[3,0][t] S[0,0,-1][t] - kpon K[3,1][t] S[0,0,-1][t] +
  koff S[0,0,0][t] + kpoff S[0,0,1][t], S[0,0,0]'[t]==
  kon K[1,0][t] S[-1,0,0][t] + kon K[2,0][t] S[0,-1,0][t] +
  kon K[3,0][t] S[0,0,-1][t] - 3 koff S[0,0,0][t] -
  kla RAFK[t] S[0,0,0][t] + dla S#RAFK[0,0,0][t],
S[0,0,1]'[t]== kon K[1,0][t] S[-1,0,1][t] +
  kon K[2,0][t] S[0,-1,1][t] + kpon K[3,1][t] S[0,0,-1][t] -
  k3 S[0,0,1][t] - 2 koff S[0,0,1][t] - kpoff S[0,0,1][t] +
```

FIG. 18
(Page 6 of 10)

```
k1 S#RAFK[0,0,0][t], S[0,1,-1][t]==
 kon K[1,0][t] S[-1,1,-1][t] + kpon K[2,1][t] S[0,-1,-1][t] -
 koff S[0,1,-1][t] - kpoff S[0,1,-1][t] -
 kon K[3,0][t] S[0,1,-1][t] - kpon K[3,1][t] S[0,1,-1][t] +
 koff S[0,1,0][t] + kpoff S[0,1,1][t],
S[0,1,0]'[t]== kon K[1,0][t] S[-1,1,0][t] +
 kpon K[2,1][t] S[0,-1,0][t] + kon K[3,0][t] S[0,1,-1][t] -
 2 koff S[0,1,0][t] - kpoff S[0,1,0][t] -
 k1a RAFK[t] S[0,1,0][t] + d1a S#RAFK[0,1,0][t],
S[0,1,1]'[t]== kon K[1,0][t] S[-1,1,1][t] +
 kpon K[2,1][t] S[0,-1,1][t] - k3 S[0,0,1][t] +
 kpon K[3,1][t] S[0,1,-1][t] - k5a S[0,1,1][t] -
 koff S[0,1,1][t] - 2 kopff S[0,1,1][t] + k1 S#RAFK [0,1,0][t],
S[0,2,-1]'[t]== kon K[1,0][t] S[-1,2,-1][t] +
 kpon K[2,2][t] S[0,-1,-1][t] - k7 S[0,2,-1][t] -
 koff S[0,2,-1][t] - kpoff S[0,2,-1][t] -
 kon K[3,0][t] S[0,2,-1][t] - kpon K[3,1][t] S[0,2,-1][t] +
 koff S[0,2,0][t] + kpoff S[0,2,1][t],
S[0,2,0]'[t]== kon K[1,0][t] S[-1,2,0][t] +
 kpon K[2,2][t] S[0,-1,0][t] + kon K[3,0][t] S[0,2,-1][t] -
 k7 S[0,2,0][t] - 2 koff S[0,2,0][t] - kpoff S[0,2,0][t] -
 k1a RAFK[t] S[0,2,0][t] + d1a S#RAFK[0,2,0][t],
S[0,2,1]'[t]== kon K[1,0][t] S[-1,2,1][t] +
 kpon K[2,2][t] S[0,-1,1][t] + k5a S[0,1,1][t] +
 kpon K[3,1][t] S[0,2,-1][t] - k7 S[0,2,1][t] -
 koff S[0,2,1][t] - 2 kpoff S[0,2,1][t] + k1 S#RAFK[0,2,0][t],
S[1,-1,-1]'[t]== kpon K[1,1][t] S[-1,-1,-1][t] -
 kpoff S[1,-1,-1][t] + kon K[2,0][t] S[1,-1,-1][t] -
 kpon K[2,1][t] S[1,-1,-1][t] - kpon K[2,2][t] S[1,-1,-1][t] -
 kon K[3,0][t] S[1,-1,-1][t] - kpon K[3,1][t] S[1,-1,-1][t] +
 koff S[1,-1,0][t] + kpoff S[1,-1,1][t] + koff S[1,0,-1][t] +
 kpoff S[1,1,-1][t] + kpoff S[1,2,-1][t],
S[1,-1,0]'t]== kpon K[1,1][t] S[-1,-1,0][t] +
 kon K[3,0][t] S[1,-1,-1][t] - koff S[1,-1,0][t] -
 kpoff S[1,-1,0][t] - k1a RAFK[t] S[1,-1,0][t] -
 kon K[2,0][t] S[1,-1,0][t] - kpon K[2,1][t] S[1,-1,0][t] -
 kpon K[2,2][t] S[1,-1,0][t] + koff S[1,0,0][t] +
 kpoff S[1,1,0][t] + kpoff S[1,2,0][t] + d1a S#RAFK[1,-1,0][t],
S[1,-1,1]'[t]== kpon K[1,1][t] S[-1,-1,1][t] +
 kpon K[3,1][t] S[1,-1,-1][t] - 2 kpoff S[1,-1,1][t] -
 kon K[2,0][t] S[1,-1,1][t] - kpon K[2,1][t] S[1,-1,1][t] -
 kpon K[2,2][t] S[1,-1,1][t] + koff S[1,0,1][t] +
 kpoff S[1,1,1][t] + kpoff S[1,2,1][t] + k1 S#RAFK[1,-1,0][t],
S[1,0,-1]'[t]== kpon K[1,1][t] S[-1,0,-1][t] +
 kon K[2,0][t] S[1,-1,-1][t] -  koff S[1,0,-1][t] -
 kpoff S[1,0,-1][t] - kon K[3,0][t] S[1,0,-1][t] - kpon K[3,1][t]
  S[1,0,-1][t] + koff S[1,0,0][t] + kpoff S[1,0,1][t],
S[1,0,0]'[t]==kpon K[1,1][t] S[-1,0,0][t] +
 kon K[2,0][t] S[1,-1,0][t] + kon K[3,0][t] S[1,0,-1][t] -
 2 koff S[1,0,0][t] - kpoff S[1,0,0][t] -
 k1a RAFK[t] S[1,0,0][t] + d1a S#RAFK[1,0,0][t], S[1,0,1]'[t]==
 kpon K[1,1][t] S[-1,0,1][t] + kon K[2,0][t] S[1,-1,1][t] +
```

FIG. 18

(Page 7 of 10)

```
          kpon K[3,1][t] S[1,0,-1][t]  - k3 S[1,0,1][t] -
     koff S[1,0,1][t] - 2 kpoff S[1,0,1][t] + k1 S#RAFK[1,0,0][t],
S[1,1,-1]'[t]==kpon K[1,1][t] S[-1,1,-1][t] +
     kpon K[2,1][t] S[1,-1,-1][t] - 2 kpoff S[1,1,-1][t] -
     kon K[3,0][t] S[1,1,-1][t] - kpon K[3,1][t] S[1,1,-1][t] +
     koff S[1,1,0][t] + kpoff S[1,1,1][t],
S[1,1,0]'[t]==kpon K[1,1][t] S[-1,1,0][t] +
     kpon K[2,1][t] S[1,-1,0][t] + kon K[3,0][t] S[1,1,-1][t] -
     koff S[1,1,0][t] - 2 kpoff S[1,1,0][t] -
     k1a RAFK[t] S[1,1,0][t] + d1a S#RAFK[1,1,0][t],
S[1,1,1]'[t]==kpon K[1,1][t] S[-1,1,1][t] +
     kpon K[2,1][t] S[1,-1,1][t] + k3 S[1,0,1][t] +
     kpon K[3,1][t] S[1,1,-1][t] - k5a S[1,1,1][t] -
     3 kpoff S[1,1,1][t] + k1 S#RAFK[1,1,0][t],
S[1,2,-1]'[t]== kpon K[1,1][t] S[-1,2,-1][t] +
     k7 S[0,2,-1][t] + kpon K[2,2][t] S[1,-1,-1][t] -
     k9a S[1,2,-1][t] - 2 kpoff S[1,2,-1][t] -
     kon K[3,0][t] S[1,2,-1][t] - kpon K[3,1][t] S[1,2,-1][t] +
     koff S[1,2,0][t] + kpoff S[1,2,1][t],
S[-1,2,0]'[t]== kpon K[1,1][t] S[-1,2,0][t] + k7 S[0,2,0][t] +
     kpon K[2,2][t] S[1,-1,0][t] + kon K[3,0][t] S[1,2,-1][t] -
     k9a S[1,2,0][t] - koff S[1,2,0][t] - 2 kpoff S[1,2,0][t] -
     k1a RAFK[t] S[1,2,0][t] + d1a S#RAFK[1,2,0][t],
S[1,2,1]'[t]== kpon K[1,1][t] S[-1,2,1][t] + k7 S[0,2,1][t] +
     kpon K[2,2][t] S[1,-1,1][t] + k5a S[1,1,1][t] +
     kpon K[3,1][t] S[1,2,-1][t] - k9a S[1,2,1][t] -
     3 kpoff S[1,2,1][t] + k1 S#RAFK[1,2,0][t],
S[2,-1,-1]'[t]== kpon K[1,2][t] S[-1,-1,-1][t] -
     kpoff S[2,-1,-1][t] - kon K[2,0][t] S2,-1,-1][t] -
     kpon K[2,1][t] S[2,-1,-1][t] - kpon K[2,2][t] S[2,-1,-1][t] -
     kon K[3,0][t] S[2,-1,-1][t] - kpon K[3,1][t] S[2,-1,-1][t] +
     koff S[2,-1,0][t] + kpoff S[2,-1,1][t] + koff S[2,0,-1][t] +
     kpoff S[2,1,-1][t] + kpoff S[2,2,-1][t],
S[2,-1,0]'[t]== kpon K[1,2][t] S[-1,-1,0][t] +
     kon K[3,0][t] S[2,-1,-1][t] - koff S[2,-1,0][t] -
     kpoff S[2,-1,0][t] - k1a RAFK[t] S[2,-1,0][t] -
     kon K[2,0][t] S[2,-1,0][t] - kpon K[2,1][t] S[2,-1,0][t] -
     kpon K[2,2][t] S[2,-1,0][t] + koff S[2,0,0][t] +
     kpoff S[2,1,0][t] + kpoff S[2,2,0][t] + d1a S#RAFK[2,-1,0][t],
S[2,-1,1]'[t]== kpon K[1,2][t] S[-1,-1,1][t] +
     kpon K[3,1][t] S[2,-1,-1][t] - 2 kpoff S[2,-1,1][t] -
     kon K[2,0][t] S[2,-1,1][t] - kpon K[2,1][t] S[2,-1,1][t] -
     kpon K[2,2][t] S[2,-1,1][t] + koff S[2,0,1][t] +
     kpoff S[2,1,1][t] + kpoff S[2,2,1][t] + k1 S#RAFK[2,-1,0][t],
S[2,0,-1]'[t]== kpon K[1,2][t] S[-1,0,-1][t] +
     kon K[2,0][t] S[2,-1,-1][t] - koff S[2,0,-1][t] -
     kpoff S[2,0,-1][t] - kon K[3,0][t] S[2,0,-1][t] - kpon K[3,1][t]
     S[2,0,-1][t] + koff S[2,0,0][t] + kpoff S[2,0,1][t],
S[2,0,0]'[t]== kpon K[1,2][t] S[-1,0,0][t] +
     kon K[2,0][t] S[2,-1,0][t] + kon K[3,0][t] S[2,0,-1][t] -
     2 koff S[2,0,0][t] - kpoff S[2,0,0][t] -
     k1a RAFK[t] S[2,0,0][t] + d1a S#RAFK[2,0,0][t], S[2,0,1]'[t]==
```

FIG. 18

```
    kpon K[1,2][t] S[-1,0,1][t]  + kon K[2,0][t] S[2,-1,1][t] +
    kpon K[3,1][t] S[2,0,-1][t] - k3 S[2,0,1][t] -
    koff S[2,0,1][t] - 2 kpoff S[2,0,1][t] + k1 S#RAFK[2,0,0][t],
S[2,1,-1]'[t]==kpon K[1,2][t] S[-1,1,-1][t] +
    kpon K[2,1][t] S[2,-1,-1][t] - 2 kpoff S[2,1,-1][t] -
    kon K[3,0][t] S[2,1,-1][t] - kpon K[3,1][t] S[2,1,-1][t] +
    koff S[2,1,0][t] + kpoff S[2,1,1][t],
S[2,1,0]'[t]==kpon K[1,2][t] S[-1,1,0][t] +
    kpon K[2,1][t] S[2,-1,0][t] + kon K[3,0][t] S[2,1,-1][t] -
    koff S[2,1,0][t] - 2 kpoff S[2,1,0][t] -
    k1a RAFK[t] S[2,1,0][t] + d1a S#RAFK[2,1,0][t],
S[2,1,1]'[t]==kpon K[1,2][t] S[-1,1,1][t] +
    kpon K[2,1][t] S[2,-1,1][t] - k3 S[2,0,1][t] +
    kpon K[3,1][t] S[2,1,-1][t] - k5a S[2,1,1][t] -
    3 kpoff S[2,1,1][t] + k1 S#RAFK[2,1,0][t],
S[2,2,-1]'[t]== kpon K[1,2][t] S[-1,2,-1][t] + k9a S[1,2,-1][t] +
    kpon K[2,2][t] S[2,-1,-1][t] - 2 kpoff S[2,2,-1][t] -
    kon K[3,0][t] S[2,2,-1][t] - kpon K[3,1][t] S[2,2,-1][t] +
    koff S[12,2,0][t] + kpoff S[2,2,1][t],
S[2,2,0]'[t]== kpon K[1,2][t] S[-1,2,0][t] + k9a S[1,2,0][t] +
    kpon K[2,2][t] S[2,-1,0][t] + kon K[3,0][t] S[2,2,-1][t] -
    koff S[2,2,0][t] - 2 kpoff S[2,2,0][t] -
    k1a RAFK[t] S[2,2,0][t] + d1a S#RAFK[2,2,0][t],
S[2,2,1]'[t]== kpon K[1,2][t] S[-1,2,1][t] +
    k9a S[1,2,1][t] + kpon K[2,2][t] S[2,-1,1][t] +
    k5a S[2,1,1][t] + kpon K[3,1][t] S[2,2,-1][t] +
    3 kpoff S[2,2,1][t] + k1 S#RAFK[2,2,0][t],
S#RAFK[-1,-1,0]'[t]== k1a RAFK[t] S[-1,-1,0][t] -
    d1a S#RAFK[-1,-1,0][t] - k1 S#RAFK[-1,-1,0][t],
S#RAFK[-1,0,0]'[t]== k1a RAFK[t] S[-1,0,0][t] -
    d1a S#RAFK[-1,0,0][t] - k1 S#RAFK[-1,0,0][t],
S#RAFK[-1,1,0]'[t]== k1a RAFK[t] S[-1,1,0][t] -
    d1a S#RAFK[-1,-1,0][t] - k1 S#RAFK[-1,1,0][t],
S#RAFK[-1,2,0]'[t]== k1a RAFK[t] S[-1,2,0][t] -
    d1a S#RAFK[-1,2,0][t] - k1 S#RAFK[-1,2,0][t],
S#RAFK[0,-1,0]'[t]== k1a RAFK[t] S[0,-1,0][t] -
    d1a S#RAFK[0,-1,0][t] - k1 S#RAFK[0,-1,0][t],
S#RAFK[0,0,0]'[t]== k1a RAFK[t] S[0,0,0][t] -
    d1a S#RAFK[0,0,0][t] - k1 S#RAFK[0,0,0][t],
S#RAFK[0,1,0]'[t]== k1a RAFK[t] S[0,1,0][t] -
    d1a S#RAFK[0,1,0][t] - k1 S#RAFK[0,1,0][t],
S#RAFK[0,2,0]'[t]== k1a RAFK[t] S[0,2,0][t] -
    d1a S#RAFK[0,2,0][t] - k1 S#RAFK[0,2,0][t],
S#RAFK[1,-1,0]'[t]== k1a RAFK[t] S[1,-1,0][t] -
    d1a S#RAFK[1,-1,0][t] - k1 S#RAFK[1,-1,0][t],
S#RAFK[1,0,0]'[t]== k1a RAFK[t] S[1,0,0][t] -
    d1a S#RAFK[1,0,0][t] - k1 S#RAFK[1,0,0][t],
S#RAFK[1,1,0]'[t]== k1a RAFK[t] S[1,1,0][t] -
    d1a S#RAFK[1,1,0][t] - k1 S#RAFK[1,1,0][t],
S#RAFK[1,2,0]'[t]== k1a RAFK[t] S[1,2,0][t] -
    d1a S#RAFK[1,2,0][t] - k1 S#RAFK[1,2,0][t],
S#RAFK[2,-1,0]'[t]== k1a RAFK[t] S[2,-1,0][t] -
```

FIG. 18
(Page 9 of 10)

```
    d1a S#RAFK[2,-1,0][t] - k1 S#RAFK[2,-1,0][t],
S#RAFK[2,0,0]'[t]== k1a RAFK[t] S[-2,0,0][t] -
    d1a S#RAFK[2,0,0][t] - k1 S#RAFK[2,0,0][t],
S#RAFK[2,1,0]'[t]== k1a RAFK[t] S[2,1,0][t] -
    d1a S#RAFK[2,1,0][t] - k1 S#RAFK[-2,1,0][t],
S#RAFK[2,2,0]'[t]== k1a RAFK[t] S[2,2,0][t] -
    d1a S#RAFK[2,2,0][t] - k1 S#RAFK[2,2,0][t],
(MAPKP,MEKP,RAFK,RAFP,K[1,0],K[1,1],[K[1,2],
 K[2,0],K[2,1],K[2,2],
 K[3,0],K[3,1], K#K[1,0,2,2],
 K#K[1,1,2,2], K#K[2,0,3,1],
 K#K[2,1,3,1], K#MAPKP[1,1],
 K#MAPKP[1,2], K#MEKP[2,1],
 K#MEKP[2,2], K#RAFK[3,0],
 K#RAFP[3,1], S[-1,-1,-1],
 S[-1,-1,0], S[-1,-1,1],
 S[-1,0,-1], S[-1,0,0],
 S[-1,0,1], S[-1,1,-1],
 S[-1,1,0], S[-1,1,1],
 S[-1,2,-1], S[-1,2,0],
 S[-1,2,1], S[0,-1,-1],
 S[0,-1,0], S[0,-1,1],
 S[0,0,-1], S[0,0,0], S[0,0,1],
 S[0,1,-1], S[0,1,0], S[0,1,1],
 S[0,2,-1], S[0,2,0], S[0,2,1],
 S[1,-1,-1], S[1,-1,0],
 S[1,-1,-1], S[1,0,-1],
 S[1,0,0], S[1,0,1], S[1,1,-1],
 S[1,1,0], S[1,1,1], S[1,2,-1],
 S[1,2,0], S[1,2,1], S[2,-1,-1],
 S[2,-1,0], S[2,-1,1],
 S[2,0,-1], S[2,0,0], S[2,0,1],
 S[2,1,-1], S[2,1,0], S[2,1,1],
 S[2,2,-1], S[2,2,0], S[2,2,1],
 S#RAFK[-1,-1,0], S#RAFK[-1,0,0],
 S#RAFK[-1,1,0], S#RAFK[-1,2,0],
 S#RAFK[0,-1,0], S#RAFK[0,0,0],
 S#RAFK[0,1,0], S#RAFK[0,2,0],
 S#RAFK[1,1,0], S#RAFK[1,0,0],
 S#RAFK[1,1,0], S#RAFK[1,2,0],
 S#RAFK[2,-1,0], S#RAFK[2,0,0],
 S#RAFK[2,1,0], S#RAFK[2,2,0]}}
```

FIG. 18

(Page 10 of 10)

AUTOMATED METHODS FOR SIMULATING A BIOLOGICAL NETWORK

This application claims priority under 35 USC 119(e) to U.S. provisional application Ser. No. 60/247,174 filed Nov. 10, 2000, the entire contents of which are incorporated herein by reference.

This invention was made in part with government support under Contract No. N00014-97-1-0422 awarded by the Office of Naval Research. The government has certain rights in this invention.

The computer listing files contained on the compact discs filed along with this specification are incorporated by reference in their entirety. The computer listing files contained on the compact disks include the following: Cellerator Pallete.nb, 30 kb, created Nov. 7, 2001; Cellerator Pallete.txt, 30 kb, created Nov. 7, 2001; cellatorl.nb, 1023 kb, created Nov. 6, 2001; Cellerator1.txt, 1023 kb, created Nov. 6, 2001; cellerator2.nb, 944 kb, created Nov. 6, 2001; Cellerator2.txt, 944 kb, created Nov. 6, 2001; cellerator3.nb, 371 kb, created Nov. 6, 2001; and Cellerator3.txt, 371 kb, created Nov. 6, 2001. The 2 compact discs filed herewith are identical in contents, each containing the above-mentioned files.

BACKGROUND OF THE INVENTION

1. Field of the Invention

The invention relates generally to computer simulations of biological networks.

2. Background Information

In the past few decades the rapid gain of information about intracellular signal transduction and genetic networks has led to the view of regulatory biomolecular circuits as highly structured multi-component systems that have evolved to perform optimally in very uncertain environments. This emergent complexity of biochemical regulation necessitates the development of new tools for analysis, most notably computer assisted mathematical models. Computer modeling has proved to be of crucial importance in the analysis of genomic DNA sequences and molecular dynamics simulations and is quickly becoming an indispensable tool in biochemical and genetic research. In the past it has been necessary to manually translate chemical networks into differential equations and then solve them numerically.

Several platforms have been developed that enable biologists to do complex computational simulations of various aspects of cellular signaling and gene regulatory networks. However, these new modeling environments have not been widely utilized in the biological research community. Among the reasons for this lack of acceptance is that the modeling interface is relatively inaccessible for the typical classically-trained geneticist or biochemist. Instead of cartoon representations of signaling pathways in which activation can be represented simply by an arrow connecting two molecular species, users are often asked to write specific differential equations or choose among different modeling approximations. Even for fairly modest biomolecular circuits such a technique would involve explicitly writing dozens (or even hundreds) of differential equations, a job that can be tedious, difficult, and highly error prone, even for an experienced modeler. Thus, there is a strong need for a modeling interface that automatically converts a cartoon- or reaction-based biochemical pathway description into a mathematical representation suitable for the solvers built into various currently existing software packages.

In addition to being more accessible to a broader research community, a tool allowing the automatic generation of mathematical models would facilitate the modeling of complex networks and interactions. For example, in intracellular signal transduction it is not uncommon to find multi-molecular complexes of modifiable proteins. The number of different states, along with the number of equations required to fully describe the dynamics of such a system, increases exponentially with the number of participating molecules or classes of molecules. One typical complex is a scaffold complex involved in MAPK cascades. It is often the case that the dynamics of each state is of interest. A modeler then faces the unpleasant, and potentially error prone task, of writing dozens, if not hundreds, of equations. Therefore, there remains a need for automatic equation generation tools that can significantly ease this task.

Bhalla and Iyengar (Bhalla, U.S., and Iyengar, R., *Science* 283:381-387 (1999);) have noted the need to systematically study interacting pathways with a standardized scheme, and have described several networks with mass-action kinetics using the Genesis simulator (Bower, J. M., and Beeman. D, The book of Genesis, Springer Verlag, Berlin (1998)). However, Bhalla does not disclose a system for automatically generating a series of differential equations from a user representation of a biological network. Furthermore, this system does not provide the user flexibility to manually intervene and modify differential equations before they are solved. Furthermore, these systems are not robust enough to be utilized for modeling of virtually any biological network such as those involved in developmental systems.

SUMMARY OF THE INVENTION

The present invention provides a general approach to automatic model generation (i.e. computer simulation) for the description of biological networks, including dynamic biological networks. The methods of the present invention facilitate biological modeling via automated equation generation based on the concept of a hierarchy of canonical forms that describe biological processes at various levels of detail. At each level of hierarchy two classes of canonical forms can be identified: the input canonical form, that is used to supply information to the program, and the output canonical form that is produced by a simulator. Thus, using the methods of the present invention, a user can input a representation of a biological network using a familiar, common biological notation form and the methods automatically generate and numerically solve a series of mathematical equations based on the representation.

Biological networks and the reactions at the core of these biological networks can be loosely classified in order of their biological complexity into the following: simple chemical reactions including degradation, enzymatic reactions in solution, multi-molecular complexes with a non-trivial number of states (e.g., scaffold proteins), multiple interacting and non-overlapping pathways, transcription, translation, intracellular components, transport processes and morphogenesis. The methods and systems of the present invention utilize general canonical forms that describe these biological networks and the reactions at the heart of these biological networks. These canonical forms can be either input forms, such as chemical reactions, or output forms, such as differential equations that are automatically generated using the methods and systems of the present invention. Furthermore, the present specification identifies these canonical forms so that an efficient mapping from the input forms to the output forms can be implemented.

The methods in certain preferred embodiments include explicit output description and flexible user intervention at several steps through the model generation. This design, which allows intervention and modification of the model "on the fly" leads to increased model design flexibility and provides an immediate error correction mechanism. Furthermore, preferred embodiments of the present invention are illustrated which provide the modeling of developmental networks using an organism-as-a-graph approach using domains and fields.

The present invention provides an automated method for simulating a biological network. The method includes the following:

a) receiving initial condition values, process parameters, and a user representation of the biological network, wherein the user representation is input using one or more of a series of biological network canonical input forms, wherein each canonical input form is based on a type of biological process in the biological network;

b) generating a series of mathematical equations in an equation output canonical form based on the input representation of the biological network and the process parameters; and c) numerically solving the series of mathematical equations using the initial condition values and the process parameters, to generate a value or a table of values as a function of time for one or more output functions of the biological network, thereby simulating the biological network.

In preferred embodiments, the series of mathematical equations are a series of differential equations. Furthermore, the method can further include manually modifying the series of mathematical equations before solving the series of mathematical equations.

In certain aspects of the methods of the present invention, the generating a series of mathematical equations comprises generating a hierarchical arrangement of canonical input forms and associated canonical output forms from the input representation and the process parameters, wherein a level of the hierarchical arrangement includes the series of mathematical equations. In preferred embodiments of these aspects, the canonical output forms can be modifiable by a user at each level of the hierarchical arrangement. Typically, the series of mathematical equations and the value for one or more outputs are generated automatically. In certain preferred embodiments, the biological network is a developmental network. The biological network can include a cell and its progeny, and the method can provide a representation of an organism as a graph, wherein the graph comprises a list of nodes, a list of links, and a lineage tree. The nodes can include one or more models that include a system of differential equations and associated parameters that describe some aspect of the biological network.

The representation of the biological network in the method can include a series of graphics of a graphic user interface or a cartoon description of the biological process. Furthermore, the method can include before generating a series of mathematical equations, generating a series of chemical equation canonical input forms based on a more detailed representation of the biological network than the user representation of the biological network.

The method can further include defining a target output value and recording the input conditions that achieve this target output value, wherein the changes are automatically generated and steps a-c are automatically repeated until the target output value is attained.

In another aspect the present invention provides a computer system that includes the following:

a user interface capable of receiving and displaying initial condition values, process parameters, and a user representation of a biological network, wherein the user representation is input as a series of canonical input forms, wherein the format for each canonical input form is based on a type of biological process in the biological network;

an interpreter function capable of generating a hierarchical arrangement of canonical input forms and associated canonical output forms from the input representation and the process parameters, wherein a level of the hierarchical arrangement comprises a series of mathematical equations; and an equation solver function capable of receiving the process parameters, the initial condition values, and the series of differential equations, and solving the differential equations, thereby generating a value or a table of values as a function of time for one or more output functions The series of mathematical equations are typically differential equations.

In certain preferred embodiments of the present invention, the computer system includes a graphing function capable of receiving the value or table of values from the solver function, and generating a graph displaying the numerical values, wherein the graph is displayed on the user interface.

In certain preferred embodiments, wherein the interpreter function generates multiple levels of canonical output forms, the user interface displays the canonical output forms at every level to allow a user to modify the canonical output forms.

In another aspect, the present invention provides a method for generating revenue comprising providing access to a computer system of the invention in exchange for consideration. The consideration is typically a user fee and the computer system is accessible through a LAN or WAN such as the internet.

In another aspect, the present invention provides a computer program product for simulating a biological network comprising a computer-usable medium having a computer-readable program code for effecting the following steps within a computing system:

a) receiving initial condition values, process parameters, and a user representation of the biological network, wherein the user representation is input using one or more of a series of biological network canonical input forms, wherein the format for each canonical input form is based on a type of biological process in the biological network;

b) generating a hierarchical arrangement of canonical input forms and associated canonical output forms from the input representation and the process parameters, wherein a level of the hierarchical arrangement comprises a series of initial differential equations;

c) numerically solving the series of mathematical equations using the initial condition values and the process parameters, to generate a value or a table of values as a function of time for one or more output functions of the biological network, thereby simulating the biological network.

The computer program product can effect generating the hierarchical arrangement of canonical output forms such that the canonical output forms are modifiable by a user at each level of the hierarchical arrangement. The biological network simulated by the computer program product can be a developmental network. Furthermore, the computer program can further effect representing a developmental network of an organism as a graph, wherein the graph comprises a list of nodes representing cells, a list of links of the cells, and a lineage tree of the cells In another aspect, the present invention provides an automated method for simulating a developmental process of an organism. The method includes the following steps:

a) receiving initial condition values and process parameters for the developmental process of the organism;

b) representing the organism or a tissue within the organism by a graph data structure, wherein the graph data structure includes:

i) a list of links, each link representing the interaction between two cells;

ii) a lineage tree recording the family tree of cell birth for the cells represented by the list of links; and iii) a list of nodes, each node representing a cell of the cells represented by the list of links, with an embedding describing the location of the cell in Cartesian coordinates and a set of differential equations describing the time evolution of the location of the cell, the differential equations including the initial condition values and process parameters, each node having a model that includes a system of differential equations and associated parameters describing the developmental process; and c) repeatedly solving the set of differential equations in a series of steps for a defined number of steps, wherein after each step results are generated and compared to a threshold to determine whether the developmental process has reached a trigger point for changing the number of nodes in the list of nodes, thereby simulating the developmental process.

A method according to this aspect of the invention preferably further includes:

d) graphing the nodes using the Cartesian coordinates.

The developmental process can be, for example, cell division, wherein reaching the trigger point adds a new node to the list of nodes.

The developmental process can be, for example, cell death, wherein reaching the trigger point removes node from the list of nodes.

The developmental process described by the differential equations can be a cell cycle pathway checkpoint, or can further include, for example, a signal transduction network of the cell. Preferably, each node is numbered as it is added to the graph data structure.

BRIEF DESCRIPTION OF THE DRAWINGS

FIG. 3 provides canonical form for glycolysis reactions and corresponding ODEs generated by Cellerator™, a computer system for performing preferred embodiments of the methods of the present invention.

FIG. 8 provides Cellerator™ arrows (i.e., an example of specific chemical formula depictions), generated ODEs, and results of numerical integration for the mitotic oscillator (equations (76) to (79)). The interpret functions returns the differential equations; the run function returns Mathematica® interpolating functions and/or code in SBML, C, FORTRAN, MATHML, XML, or HTML.

FIG. 9 describes a graph structure used in certain preferred methods of the present invention, for a unicellular organism with a minimal developmental system. The indices on the variables indicate cell number.

FIG. 12 provides an exemplary Cellulator™ command syntax.

FIG. 13 provides an exemplary Cellulator™ command syntax.

FIG. 14 provides the implementation of automatic generation of the MAP kinases activation reactions (through phosphorylation) in the scaffold in the Cellerator™ environment, a preferred environment for performing the methods of the present invention. All the possible scaffold states (species) are generated as are the transition reactions between them. The indexes in the parentheses indicate the phosphorylation status of the kinase in the corresponding position, with −1 corresponding to the absence of the kinase from the scaffold complex. K[4,1] represents the external kinase activating the first MAP kinase (MAPKKK) in the cascade.

FIG. 15 provides a flow chart representing an automated method for simulating a biological network according to the present invention and illustrates that although a computer program is used to generate and solve the series of initial mathematical equations, preferably a user can intervene and modify canonical output forms generated throughout the process.

FIGS. 17a-d provides an output containing an initial set of reactions for a MAPK cascade on a Scaffold generated by the Cellerator™ program after the input described in Example 1, wherein the list of reactions are assigned to the variable c.

FIGS. 18a-j provides a set of differential equations generated by the Cellerator™ program after the input described in Example 1, wherein the list of differential equations are assigned to the variable s.

DETAILED DESCRIPTION OF THE INVENTION

Figure 1:
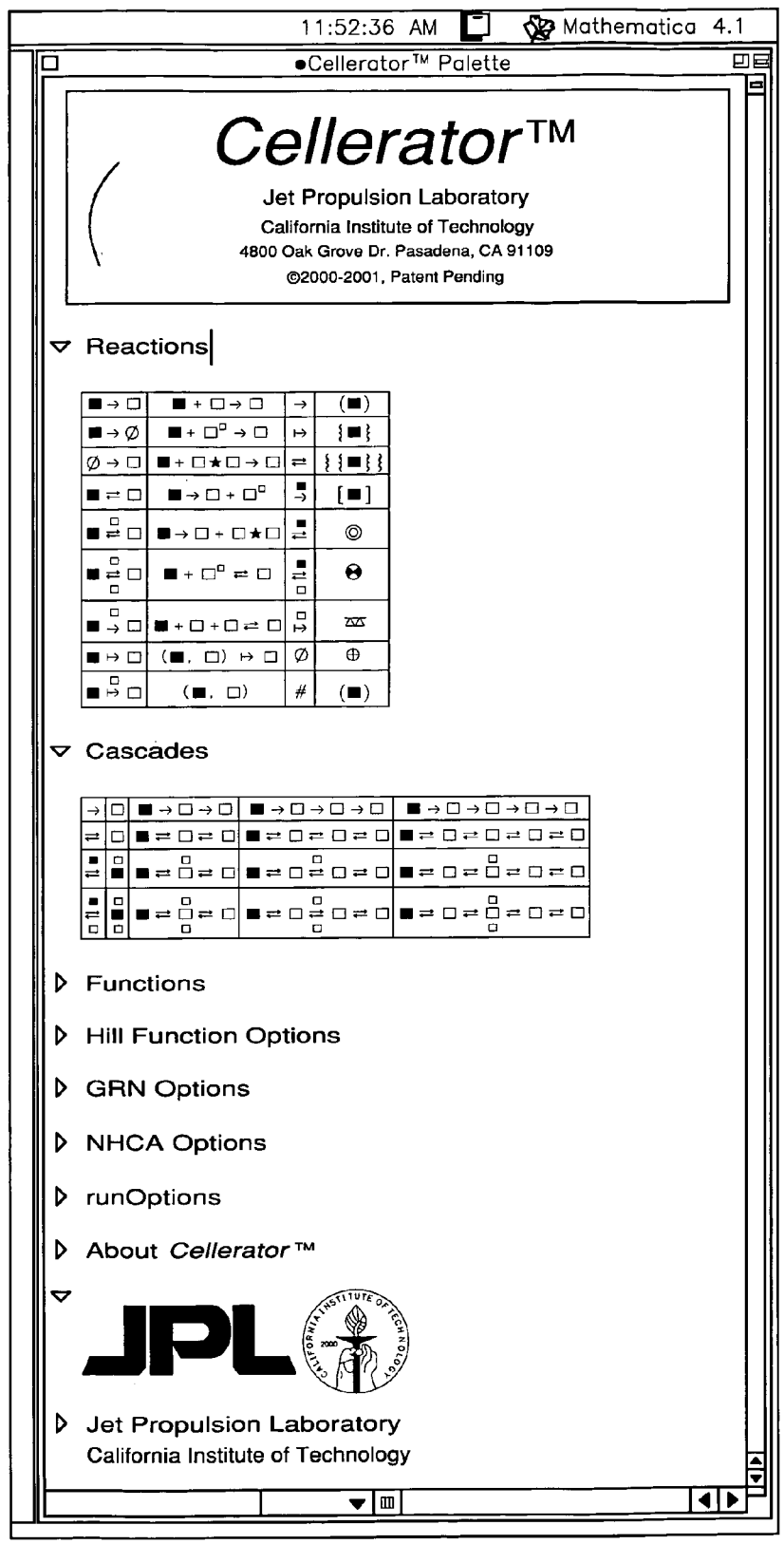
FIG. 1 illustrates a preferred user interface of the present invention. A palette is provided for selecting canonical input forms representing various reaction types.

The present invention provides an automated method for simulating a biological network. The method includes the following steps:
  a) receiving initial condition values, process parameters, and a user representation of the biological network, wherein the user representation is input using one or more of a series of biological network canonical input forms, wherein each canonical input form is based on a type of biological process in the biological network;
  b) generating a series of mathematical equations in an equation output canonical form based on the input representation of the biological network and the process parameters; and
  c) numerically solving the series of mathematical equations using the initial condition values and the process parameters, to generate a value or a table of values as a function of time for one or more output functions of the biological network, thereby simulating the biological network.

Biological networks and the detailed chemical processes that occur within them, are described by the methods and systems of the present invention utilizing general canonical forms. These canonical forms can be either input forms, such as chemical reactions, or output forms, such as differential equations that are automatically generated using the methods and systems of the present invention. Biological networks are generally expressed in terms of the biochemical cascades that occur. The chemical reactions of these biochemical cascades constitute the core input forms of the present invention; the corresponding differential equations constitute the core output forms. Differential equations can be thought of as output because they can be passed on to solver and/or optimizer modules to handle.

Typically, as shown in step 10 of FIG. 15, to initiate the methods of the present invention, a user inputs a user representation of the biological network which is received by a computer program performing the methods of the present invention. The representation of the biological network can include, for example, a series of graphics of a graphical user interface, reaction scheme diagrams, a block diagram, and/or a cartoon description of the biological process. For example, Ichikawa discusses a palette-based graphical user interface for describing small biochemical systems and translating them into differential equations that can be subsequently solved with other utilities (Ichikawa, K., *Bioinformatics*, 17:483-484 (2001)). According to the methods of the present invention, the accuracy of the user representation can be confirmed by comparing results of the automated methods of the present invention with results from experiments performed on living systems. Therefore, the present invention provides a method to confirm the accuracy of models of biological networks.

The user representation of the biological network is input using one or more of a series of biological network canonical input forms. The biological network canonical input forms may take on various forms as discussed above. However, each canonical input form is based on a type of biological process, typically a type of biological reaction, in a biological network being simulated. For example, different canonical input forms can be used to represent a reaction in which a complex is formed, a dissociation reaction, a conversion, a degradation reaction, transcription regulation, an enzyme kinetic reaction, Hill function, or non-hierarchical cooperative activation reactions. Mathematical equations are then automatically generated by a computer program performing a method of the present invention, based on the type of reaction received by the program, according to the rules described herein. Typically, the mathematical equations are ordinary differential equations based on the canonical input form.

The series of biological network canonical input forms and the equation output canonical forms in preferred embodiments are part of a hierarchy of canonical input forms and related canonical output forms that describe a biological network at various levels of detail. In fact, preferred methods of the invention are based on the concept of a hierarchy of canonical forms that describe biological processes at various levels of detail. These preferred methods are based on the fact that biological systems are usually described in terms of signal transduction networks (STN). Nodes in an STN typically represent chemical species (e.g., nucleic acids, proteins, etc.) while links represent interactions between the species. Such networks are inherently hierarchical. Nodes may represent anything ranging from single molecules (e.g., particular enzymes, receptors) or ubiquitous modules (e.g., MAPK cascades, transcription complexes, etc.) to extremely complex processes such as mitosis (see, for example, Kohn, K. W., *Mol. Biol. Cell.* 10:2703-2734 (1999)). At the highest level of abstraction an input canonical form is pictorial (e.g., a cartoon drawn on the screen using some sort of GUI), while an output canonical form is a complete set of differential equations describing the network.

At each level of hierarchy the two classes of canonical forms can be identified: the input canonical form, that is used to supply information to the program, and the output canonical form (OCF) that is automatically generated by an interpreter function, also called a simulator. Because of this hierarchical arrangement, the step 20 of generating a series of mathematical equations in an equation output canonical form based on the input representation of the biological network and the process parameters, can include generating a hierarchical arrangement of canonical input forms and associated canonical output forms from the input representation and the process parameters. In these embodiments, a final level of the hierarchical arrangement comprises a series of initial mathematical equations. Therefore, the automated methods of the present invention can generate a series of hierarchical levels of canonical output forms that are used to automatically generate a next level of canonical output forms.

The methods of the present invention are based on the proposition that there is a one-to-one relationship between each class of interaction (link) in an STN and a hypothesized formal (i.e., mathematical) description of that interaction. The methods of the present invention can represent nodes with variables (e.g., chemical concentrations) and links with specialized chemical reaction depictions. The method can include before generating a series of initial mathematical equations, generating a series of chemical equation canonical input forms providing a more detailed representation of the biological network than the user representation of the biological network. Both of these steps are performed automatically typically by a computer program performing the methods of the present invention.

Typically, the series of mathematical equations generated in step 20 of the methods of the present invention are a series of differential equations. However, other types of equations can be used either in place of differential equations or along with differential equations. For example, stochastic equations, stochastic differential equations, or differential equations and simple algebraic expressions representing some algebraic constraints representing, for example, random noise can be used. The random noise represented by these equations includes, for example, diffusion rates or thermal noise. The algebraic constraints can specify some algebraic equations that are also true (e.g., say x+y+z=0) as well as some test conditions (such as If (x+y>z) then (w=x) else (w=y).

As described above, the concept of a canonical form is central to the methods and systems of the present invention. At each level of information processing, typically there are both input and output canonical forms. The output forms can them be fed back into the system as input forms for the next stage of processing. The implementation of these canonical forms is platform and language dependent. It is the canonical forms themselves that are important to the methods and systems of the present invention, not their implementation. One can thus visualize a succession of canonical forms (Table 1). The various levels indicated in Table 1 are for illustration purposes only; the actual names and succession of levels is not a core element of the methods and systems.

TABLE 1

Canonical forms for different levels of the Cellerator™ paradigm.

| Level | Input Form | Output Form |
| --- | --- | --- |
| Web Interface | Web Database Record | Graph-Representation of STN |
| User Interface | Cartoon Figure | Graph representation of STN |
| Notebook Interface | Cellerator™ Arrow | Chemical Equations |
| Translator | Chemical Equations | DAEs, ODEs |
| Solver | DAEs, ODEs | Numerical Solutions |
| Simulation Kernel | Numerical Solutions plus Graph | Modified Graph |

STN: Signal Transduction Network; DAE: Differential-Algebraic Equation; ODE: Ordinary Differential Equation.

Virtually any type of biological network can be simulated using the methods of the present invention. For example, the biological network can include the following: simple chemical reactions: degradation, enzymatic reactions in solution, multi-molecular complexes with a non-trivial number of states (e.g., scaffold proteins), multiple interacting and non-overlapping pathways, transcription, translation, intracellular components, transport processes, morphogenesis, simple development systems, tissue development and development of complex multicellular organisms. These biological networks include metabolic reaction networks, catabolic reaction networks, nucleic acid synthesis reaction networks, amino acid synthesis networks, energy metabolism and so forth. Other types of biological reaction networks include cell signaling networks, cell cycle networks, genetic networks involved in regulation of gene expression, such as operon regulatory networks, and actin polymerization networks that generate portions of the cytoskeleton. Most of the major cell functions rely on a network of interactive biological reactions.

A wide variety of biologically-based interactions can be represented as specialized chemical reaction depictions, a type of canonical input form used in preferred embodiments of the methods and systems of the present invention. The chemical reaction depiction S S⇌P, for example, can be the input canonical form for a catalytic reaction in which species E facilitates the conversion of S into P. Output canonical forms can take either of two forms, selected at the user's discretion: lists of biochemical reactions, or systems of ordinary differential equations (ODEs). The corresponding OCF for the catalytic reaction, for example, can be either a system of ODEs as determined by the law of mass action, or a list of chemical reactions such as S+E→SE, etc. A slightly different specialized equation form A↦B can indicate that the ODEs are determined by steady state kinetics (e.g., Michaelis-Menten) rather than mass-action equations. A similar notation A↦B can mean that A facilitates the transcription of B.

Although a computer system 100 is used to generate the canonical output forms, and typically canonical input forms from these canonical output forms, the methods of the present invention, in certain preferred embodiments, allow explicit output description at each level so that a user 110 can modify the equations at any stage desired. Users can thus manually modify the ODEs or chemical equations, or add additional constraints in the form of differential, algebraic, or chemical equations. For example, the series of initial mathematical equations, in certain preferred embodiments, can be modified before they are solved. As another example, where the method generates a series of detailed chemical equations as a canonical output form based on a the user representation of the biological network, the method can be implemented so that a user can manually modify the series of detailed chemical equations.

Output functions of the methods of the present invention include virtually any output function of biology. Output functions include, but are not limited to, growth rate, cellular relationships and interactions during development, changes in protein phosphorylation patterns over time, changes in biomass over time, and yields of biomolecules such as proteins, carbohydrates, antibiotics, vitamins, amino acids, fermentation products, such as lactate production, yields of chiral compounds and other low molecular weight compounds, and the maximal internal yields of key co-factors, such as energy carrying ATP or redox carrying NADPH and NADH.

Figure 2:
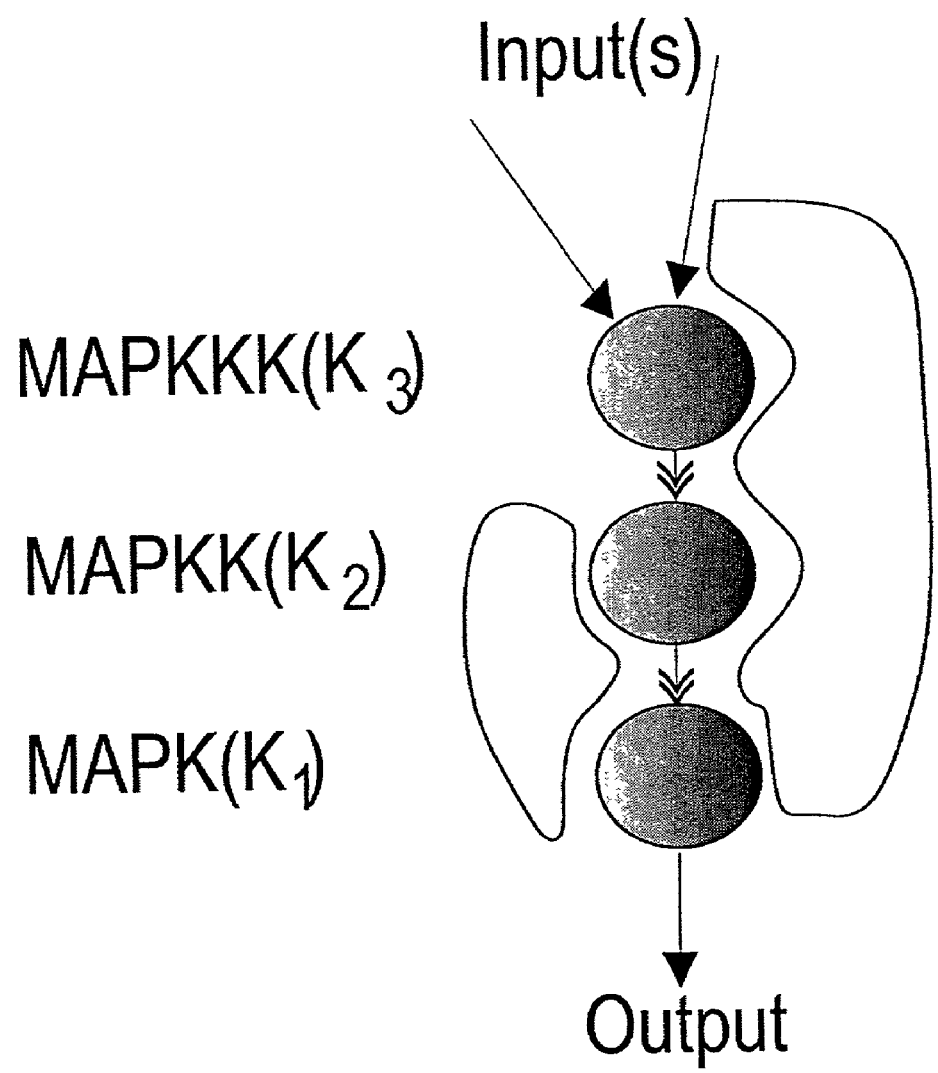
FIG. 2 illustrates the topology of MAPK signaling cascade. Each double arrow represents activation through dual phosphorylation. Two and three-member scaffolds have been identified experimentally and are depicted here.

The user representation of the biological network may be an informal, broadly focused, cartoon-based representation of the biological network. FIG. 2 is an example of a cartoon-based representation that can be used to represent a biological network. Certain shapes, such as ovals can be used to represent proteins in a biological network. Activation, such as phosphorylation, can be indicated by arrows, for example double, triple, etc. phosphorylation can be indicated by double, triple, etc. arrows, respectively. Multimember complexes, such as scaffolds, can be represented by lines or figures that connect or horizontally or vertically overlap proteins of the multimember complex (as shown in FIG. 2). A computer program performing a method of the present invention can utilize this cartoon input form to automatically derive a series of canonical forms that represent the chemical reactions represented in the cartoon, and/or can automatically generate a series of initial mathematical equations from the cartoon.

In certain embodiments of the present invention, rather than describing specific details of the biological network, the user can input the user representation of the biological network by selecting the biological network from a listing of biological networks appearing on a computer display provided by a computer system capable of performing the methods of the present invention. A detailed representation of the biological network selected by the user may be obtained by the computer system by accessing a database containing such information. Additionally, a computer system performing the methods of the present invention may include a listing, such as a listing stored in a database, of other biological networks, and may search the listing to identify other biological networks that interact with the biological network selected by the user. The computer system may utilize information regarding the other biological networks in generating a value for one or more output functions of the biological network using the methods of the present invention. The listing of biological networks may be provided by a provider of a computer program capable of executing the methods of the present invention. Furthermore, the methods of the present invention can include a step whereby user representations of biological networks are stored in a listing of biological networks which is searched for interactions with an on-test biological network as described above.

Initial condition values received in step 10 include any value that is important to determine product formation of a biological reaction. Such values include, for example, concentrations or quantities of reactants, or enzymes, pH, temperature, cellular geometry, etc. For example, where the biological network is cell divisions of a single cell system, initial condition values are specified, for example, for cell geometry and initial concentrations of reactants such as proteins involved in mitotic regulation (e.g. cyclins, CDC2 kinase, cyclin protease, etc.).

Process parameters received in step 10 include rate constants, connection strengths, thresholds for activation, cooperativity, spatial geometry including cell position, etc.

The methods of the present invention can be extended from a simulation tool to a learning tool in which target output values (i.e. desired outputs) can be specified to obtain the parameters and therefore the model which leads to the target output values (Rienitz, J., et al. "A Connectionist Model of the Drosophila Blastoderm," in The Principles of Organization in Organisms, (eds. Jay E. Mittenthal and Arthur B. Baskin, Santa Fe Institute Studies in the Sciences of Complexity, Addison-Wesley) (1992); and Reinitz J., et al., *Journal of Experimental Zoology* 271:47-56, (1995)). Thus, the method can further include defining a target value for an output function and recording the input conditions that achieve this target value for the output function, wherein changes in input conditions are automatically generated and steps a-c are automatically repeated in an iterative manner until the target output value is attained.

The method of the present invention can be used to simulate dynamic biological networks (i.e. biological networks which change over time). For these simulations, steps a-c are typically repeated after changing one or both the initial condition values, or the representation of the biological network, based on the results of the previous cycle. The cycling is typically carried out for a user defined number of cycles based on a relevant time period.

Furthermore, the present invention can be used to predict the effects of alterations of the biological network on one or more outputs of the biological network. Thus, the present invention can be used to predict the effect of small organic compounds or other on-test compounds on the biological network to assist in biopharmaceutical product development.

Figure 16:
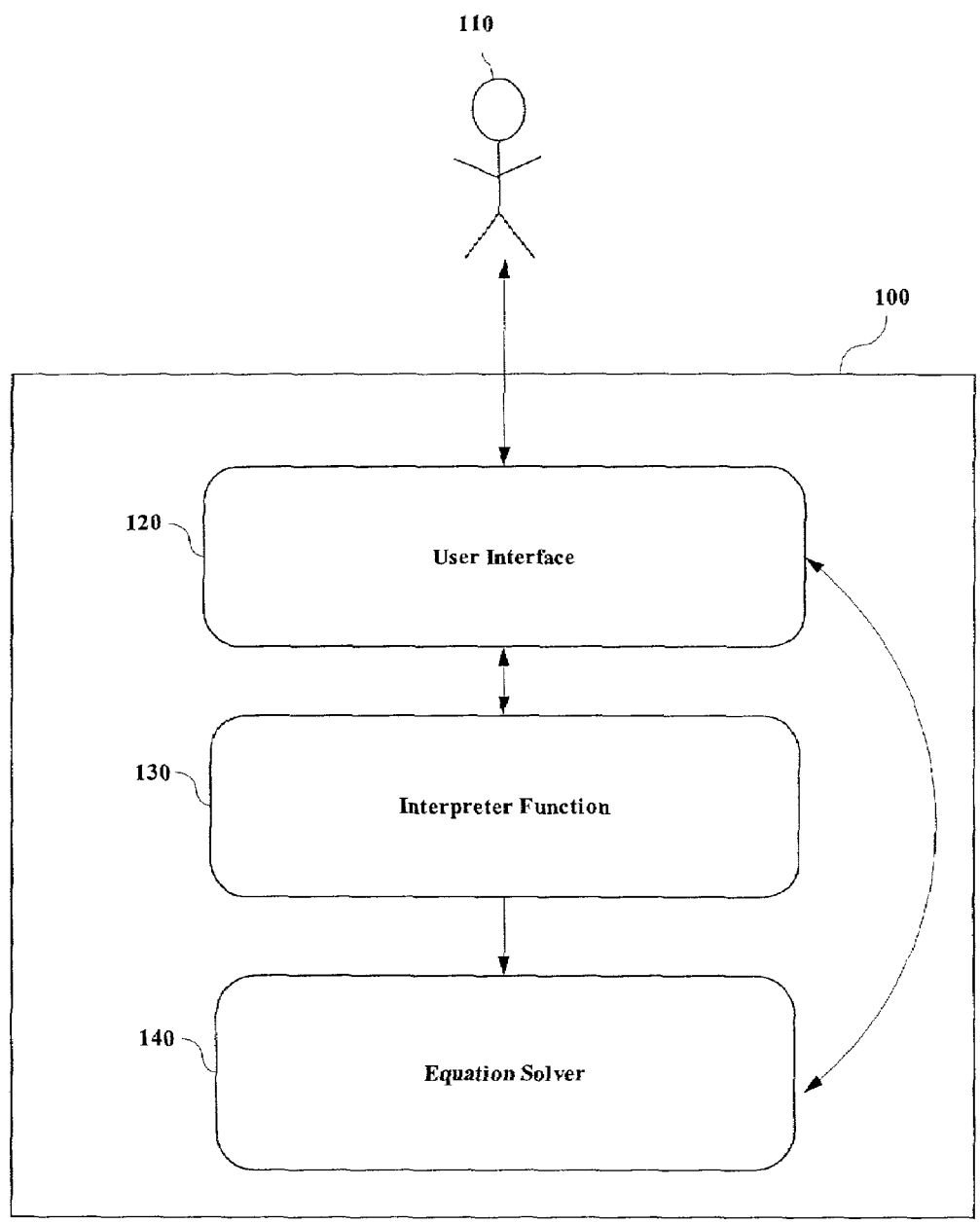
FIG. 16 provides a diagrammatic representation of a computer system for performing a method for simulating a response of a biological network.

The method for simulating a response of a biological network (FIG. 15) is carried out using a computer system 100, as schematically represented in FIG. 16, which itself represents another aspect of the present invention. The computer system typically includes a user interface capable of receiving and displaying initial condition values, process parameters, and a user representation of a biological network, from a user. The user representation is input as a series of canonical input forms. The computer system 110 includes an interpreter function 130 for performing step 20. That is, the interpreter function 130 is capable of receiving the canonical input forms and the process parameters, and generating at least a first level of output canonical forms, and typically multiple levels of output canonical forms, based on the input canonical forms. The output canonical forms include a series of mathematical equations, typically as a final level of canonical output forms, generated from the user representation of the biological network and the process parameters. In certain preferred embodiments, the user interface displays the canonical output forms at every level, and allows a user 110 to modify these canonical output forms.

The computer system 100 includes an equation solver function 140 capable of receiving the series of initial mathematical equations, the initial conditions values, and the process parameters, and generating a numerical value, typically a table of values as a function of time, for one or more output functions using the mathematical equation and the initial condition values (Step 40). This step 40 typically includes numerically solving the mathematic equations. In certain preferred embodiments of the present invention, the computer system 100 includes a graphing function, capable of receiving numerical values from the numerical solver function, and generating a graph from them which is displayed on the user interface. The computer system may also include an optimizer function which fits data to the equations, preferably differential equations, thereby determining optimal or improved values for some or all of the process parameters.

The computer systems 100 used to perform the methods of the present invention can implement a variable structure system using a commercially available pre-packaged fixed structure differential equation solver capability such as Mathematica™'s NDSolve. For example, the computer program can have a Mathematica® notebook interface and/or a graphical user interface. One of ordinary skill in the art will recognize that the translator function can be used with many different user interfaces (i.e. "front ends") as well. Furthermore, the computer system can include a graphing capability that generates graphs of the numeric values for output functions, which can be displayed on the user interface.

Typically, the user interface allows the user to input the user representation of the biological network manually, or to select the canonical input forms used in the user representation from a specialized computer input interface. The specialized computer input interface may be a GUI interface. For example, the user can input the canonical input forms that represent a biological network using a specialized palette, for example that depicted in FIG. 1. The palette can include a reaction list section 10 that includes input canonical forms that can be selected by a user to construct the specific input canonical forms that represent a biological network. The palette can be designed using commercial programs such as Mathematica® (Wolfram Research, Inc., Champaign, Ill.), etc. Palettes can also be written with any standard computer language such as, for example, C, C++, or Java, or with other programs such as MatLab (The MathWorks, Inc., Natick, Mass.), or LabView (National Instruments, Austin, Tex.). Furthermore, the palette can be designed such that it can be rearranged by the user.

One or more of the functions of the computer system of the present invention can be developed using a any of a number of currently-available tools in addition to Mathematica® (e.g., BioSpice, DBSolve, E-Cell, Genesis, Gepasi, M-Cell, Neuron, Stochsim, V-Cell, XSIM; for references see Hucka M., et al., 2 Mar. 2001, http://www.cds.Caltech.edu/erato. Preferably, the tool that is used to implement the methods and computer systems and programs of the present invention is a computer algebra program (e.g., Mathematica®). A computer algebra program tool facilitates weight-sharing and indexing, and many other "semantically deep transformations" that can be performed by the methods of the present invention during the canonical form to canonical form translations. In a preferred embodiment, the methods and systems of the present invention generate output in a standardized data transfer protocol such as the systems biology markup language (SBML) proposed by Hucka et al ("The ERATO Systems Biology Workbench: An Integrated Environment for Multiscale and Meltitheoretic Simulations in Systems Biology," in *Foundation of Systems Biology* (ed. Hiroaki Kitano) 125-44, MIT Press (2001)). Furthermore, Python script can be used to convert SBML into compilable C code.

Output canonical forms can be generated by the interpreter function in a variety of formats: for example, as specialized chemical reaction depictions, Mathematica® differential equations, in C, FORTRAN, SBML (Hucka M., et al. (2001)), MATHML, or HTML. If desired, the user can also solve the equations numerically (e.g., using Mathematica®'s NDSolve Wolfram, S., The Mathematica® Book. Fourth Edition. Cambridge University Press, New York (1999)).

The computer system used to perform the methods of the present invention can include a database of information regarding one or more biological networks and biological processes within the biological networks. This information can include identification of biomolecular reactants, products, cofactors, enzymes, rates of reactions, coenzymes, etc. involved in a biochemical network. This information can include the stoichiometric coefficients that indicate the number of molecules of a compound that participates in a particular biochemical reaction. This information can include details of multimeric reactions and interacting and overlapping pathways, as well as information regarding locations of reactants, (i.e. if they are in a membrane, in the cytoplasm, or inside an organelle such as the mitochondria). The information can also include experimentally derived or calculated rates of reactions under various conditions. Furthermore, the database can include any type of biological sequence information that pertains to a biological network. Finally, the data in the database is preferably stored in a standardized form that is or can be rapidly converted to, canonical input forms of the present invention.

The database can be a flat file database or a relational database. The database can be an internal database, or an external database that is accessible to users, for example a public biological sequence database, such as Genbank or Genpept. An internal database is a database maintained as a private database, typically maintained behind a firewall, by an enterprise. An external database is typically located outside a user's local computer network, and is typically maintained by a different entity than that which maintains a user's computer and local network. Many external public biological information databases are available and can be used with the present invention. For example, Kyoto Encyclopedia of Genes and Genomes (KEGG)(Available at http://www.genome.adjp/KEGG/), EcoCyc and Metacyc (Available at http://malibu.ai.sri.com/), EMG (Available at http://emip.mcs.anl.gov/), BRENDA (Available at http://www.brenda.uni-koeln.de/), etc., as well as many of the biological sequence databases available from the National Center for Biological Information (NCBI), such as Genbank. These databases can be used in the methods of the present invention.

The function of a computer system of the present invention typically includes a processing unit that executes a computer program product, itself representing another aspect of the invention, that includes a computer-readable program code embodied on a computer-usable medium and present in a memory function connected to the processing unit. The memory function can be ROM or RAM, for example.

The computer system used to perform the automated methods of the present invention can be a stand-alone computer or a conventional network system including a client/server environment, and optionally one or more database servers. A number of conventional network systems, including a local area network (LAN) or a wide area network (WAN), are known in the art. Additionally, client/server environments, database servers, and networks are well documented in the technical, trade, and patent literature. For example, the server can run on an operating system such as UNIX, running a World Wide Web application, and a World Wide Web Server.

The computer program product that is read and executed by the processing unit of the computer system of the present invention, includes a computer-readable program code embodied on a computer-usable medium. The program code is capable of effecting the following steps within a computing system:

a) receiving initial condition values, process parameters, and a user representation of the biological network, wherein the user representation is input using one or more of a series of biological network canonical input forms, wherein the format for each canonical input form is based on a type of biological process in the biological network;

b) generating a hierarchical arrangement of canonical input forms and associated canonical output forms from the input representation and the process parameters, wherein a level of the hierarchical arrangement comprises a series of initial differential equations; and c) numerically solving the series of mathematical equations to generate a value or a table of values as a function of time for one or more output functions of the biological network by inputting the initial condition values and the process parameters into the solved mathematical equations, thereby simulating the biological network.

The computer program product can effect generating the hierarchical arrangement of canonical output forms such that the canonical output forms are modifiable by a user at each level of the hierarchical arrangement. The biological network simulated by the computer program product can be a developmental network. Furthermore, the computer program can further effect representing a developmental network of an organism as a graph, provides a representation an organism as a graph, wherein the graph comprises a list of nodes representing cells, a list of links of the cells, and a lineage tree of the cells.

In another aspect, the present invention provides a method for generating revenue comprising providing access to the computer system of the present invention in exchange for consideration. The consideration is typically a user fee, for example a per-use fee or a periodical fee for access to the computer system. For example, the computer system can be accessed by a user via a LAN or a WAN, such as the Internet.

The following section identifies core biochemical reactions that describes various biological processes, the representation of these core biochemical reactions as specialized chemical reaction depictions, a type of canonical input form, and the interpretation of these core chemical reactions as differential equations. A fundamental library of simple chemical reactions can be quickly developed; such reactions take the form $$\sum_{X_i \in S' \subset S} X_i \xrightarrow{k} \sum_{Y_i \in S'' \subset S} Y_i \qquad (1)$$

where S is a set of reactants and S' and S" are (possible empty and possibly non-distinct) subsets of S and k is a representation of the rate at which the reaction proceeds. In general there are rarely more than two elements in either S' or S" but it is possible for there to be more. For example, all of the following chemical reactions fall into this form:

$A+B \rightarrow C=AB$ complex formation $C=AB \rightarrow A+B$ dissociation $A \rightarrow B$ conversion $A \rightarrow \phi$ degradation $\phi \rightarrow A$ creation (e.g., through transcription) (2)

Enzyme kinetic reactions, which are usually written as $S+E \rightarrow P+E$ (3)

where E is an enzyme that facilitates the conversion of the substrate S into the product P, would also fall into this class. More generally, equation 3 is a simplification of the cascade $S+E \leftrightarrow SE \rightarrow S+P$ (4)

where the bi-directional arrow indicates that the first reaction is reversible. Thus (4) is equivalent to the triplet of reactions $\{S+E \rightarrow SE, SE \rightarrow S+E, SE \rightarrow S+P\}$ (5)

The reactions (4) or (5) can be written compactly with the following double-arrow notation $$S \overset{E}{\Rightarrow} P \qquad (6)$$

which should be read as "the conversion of S to P is catalyzed by an enzyme E." If there is also an second enzyme, G, that can catalyze the reverse reaction $$P \overset{G}{\Rightarrow} S = \{P + G \rightarrow GP, GP \rightarrow G + P, GP \rightarrow G + S\} \qquad (7)$$

we further use the double-double arrow notation $$S \overset{E}{\underset{G}{\Leftrightarrow}} P \qquad (8)$$

to compactly indicate the pair of enzymatic reactions given by (6) and (7). The enzyme above the arrow always facilitates the forward reaction, and the enzyme beneath the reaction always facilitates the reverse reaction. For example, E might be kinase and G might be a phosphatase molecule. Since each of equations (6) and (7) represent a triplet of simpler reactions, we observe that the notation of equation (8) compactly presents a total of six elementary reactions, each of which is in the form given by equation (1). We therefore take equation (1) as our input canonical form for chemical reactions.

The corresponding output canonical form is given by the set of differential equations $$\tau_i \dot{X}_i = \sum_\alpha c_{i\alpha} \prod_j X_j^{n_{i\alpha j}} \qquad (9)$$

where the $\tau_i$ and $c_{i\alpha}$ are constants that are related to the rate constants; and the $n_{i\alpha j}$ represent the cooperativity of the reaction. The summation is taken over all equations in which $X_i$ appears. Multi-molecular reactions (e.g., binding to a scaffold protein) and multiple interacting and overlapping pathways are described in much the same way—there are just more reactions that must be included in our model. The canonical forms (1) and (9) can still describe each one of these reactions.

Genetic transcription and translation into proteins can be described by an extension of equation (9) to include terms of the form $$\tau_i \dot{X}_i = \prod_\beta \frac{c_{i\beta} X_\beta^{n_\beta}}{K_{i\beta}^{n_\beta} +} \qquad (10)$$

where the product runs over the various transcription factors $\{X_\beta\}$ that influence production of $X_i$. If there are any reactions of the form (1) for $X_i$ then the expression on the right side of equation (10) would be added to the right hand side of (9). In a more realistic system, a gene would be influenced by a (possibly large) set of promoter and enhancer elements $X_i$ that bind to different sites. A hierarchical model could describe this set of interactions $$\tau_i \dot{X}_i = \frac{Ju_i}{1+Ju_i} - i \qquad (11)$$

$$u_i = \prod_{\alpha \in i} \frac{1 + J_\alpha \tilde{v}_\alpha}{1 + \hat{J}_\alpha \tilde{v}_\alpha} \qquad (12)$$

$$\tilde{v}_\alpha = \frac{\tilde{K}_\alpha \tilde{u}_\alpha}{1 + \tilde{K}_\alpha \tilde{u}_\alpha} \qquad (13)$$

$$\tilde{u}_\alpha = \prod_{b \in \alpha} \frac{1 + K_b v_{j(b)}^{n(b)}}{1 + \hat{K}_b v_{j(b)}^{n(b)}} \qquad (14)$$

where i and j index transcription factors, $\alpha$ indexes promoter modules, b indexes binding sites, the function j(b) determines which transcription factor j binds at site j, the J and K are constants, and $\lambda$ is a degradation rate.

Sub-cellular components represent a higher order of biological complexity. If we assume perfect mixing each component can be treated as a separate pool of reactants which we can describe by the reaction $X_A \rightarrow X_B$ (15)

This is taken to mean that X in pool A is transported into pool B at some rate. When the concentration changes and distances involved are small such processes can be described by the canonical forms in equation (1). In large or elongated cells with long processes (such as neurons) or when the molecules have a net charge the transport process defined in equation (15) can not be described by the output canonical form (9). Instead we must modify this ordinary differential equation into a partial differential equation to allow for diffusion,

  (16)

where the $D_i$ are (possibly spatially dependent) diffusion constants for species $X_i$, $C_i$ are charge and temperature dependent constants, and V is the voltage. Other voltage and pressure dependent movement between compartments (especially those with membranes) that are controlled by channels and transport proteins could be described by including additional terms on the right hand side of equation (16) (e.g., Hodgkin-Huxley type expressions).

A reiteration and slightly modified example of the preferred input canonical forms and corresponding equations described above, is provided in the following paragraphs. Uncatalyzed mass action reaction can be represented in the methods of the present invention by the following chemical reaction notation:

$$A+B^n \rightarrow C \quad (17)$$

where B is optional and n is an optional positive integer indicating that one molecule of A combines with n molecules of B to form one molecule of C. Either A or C may be the empty set (∅). The term $B^n$ can also be written as nB. Two-way reactions can be written with the "double arrow" as $$A+B^n \rightleftharpoons C \quad (18)$$

The general syntax for generating ODEs from reactions is $$\text{interpret}[r] \quad (19)$$

where r is a list of reactions of the form $$r=\{\{\text{reaction,rates}\}, \{\text{reaction,rates}\}, \ldots\} \quad (20)$$

Several examples of the translation are illustrated in table 2.

Table 2. Specialized chemical reaction depictions and differential equation interpretations for uncatalyzed reactions.

TABLE 2

Specialized chemical reaction depictions and differential equation interpretations for uncatalyzed reactions.

| Reaction Syntax | ODE Interpretation |
|---|---|
| $\{S \rightarrow P, k\}$ | $S' = -P' = -kS$ |
| $\{A + B \rightarrow C, k\}$ | $A' = B' = -C' = -kAB$ |
| $\{A + B^n \rightarrow C, k\}$ | $A' = B' = -C' = -kAB^n$ |
| $\{A \leftrightarrows B, k_f, k_r\}$ | $A' = -B' = -k_f A + k_r B$ |
| $\{A + BFC, k_f, k_r\}$ | $A' = B' = -C' = -k_f AB = k_r C$ |
| $\{\emptyset \rightarrow A, k\}$ | $A' = k$ |
| $\{B \rightarrow \emptyset, k\}$ | $B' = -kB$ |

A catalytic reaction is any reaction in which one molecule E (for "enzyme") catalyzes the conversion S (for "source") into P (for "product"). In the most generalized form, an intermediate species (called SE) is formed,

  (21)

where a, d, and k are rate constants. The conversion of ATP into ADP by PFKA in equation (4) is an example of such a reaction. The canonical form for a catalytic reaction is

  (22)

which is translated into the canonical forms $$\{\{S+E\rightarrow SE,a\},\{SE\rightarrow S+E,d\},\{SE\rightarrow P+E,k\}\} \quad (23)$$

and interpreted as already described. If a second enzyme F catalyzes the reverse reaction

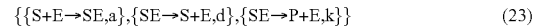  (24)

we can either add a second reaction

  (25)

or we can use the different notation

  (26)

to indicate all six reactions described by equations (22) and (25). If no intermediate compound is formed, we can write

  (27)

A summary of catalytic reactions is given in table 3, along with specialized chemical reaction depictions that represent these reactions and differential equations interpretations of these reaction depictions.

TABLE 3

Specialized chemical reaction depictions for catalyzed reactions and differential equation interpretations of these depictions.

| Reaction Syntax | ODE interpretation |
|---|---|
| $\{S \underset{}{\overset{E}{\rightleftharpoons}} P, a, d, k\}$ | $S' = -a \cdot E \cdot S + d \cdot S$<br>$P' = k \cdot (SE)$<br>$E' = -a \cdot E \cdot S + (d + k) \cdot (SE) = -(SE)'$ |
| $\{S \underset{F}{\overset{E}{\rightleftharpoons}} P, a, d, k$ | $S' = k_1 \cdot (PF) - a \cdot E \cdot S + d \cdot (SE)$<br>$P' = -a_1 \cdot F \cdot P + d_1 \cdot (PF) + k \cdot (SE)$ |
| a1, d1, k1 | $E' = -a \cdot E \cdot S + (d + k) \cdot (SE) = -(SE)'$<br>$F' = -a_1 \cdot F \cdot P + (d_1 + k_1) \cdot (PF) = -(PF)'$ |

TABLE 3-continued

Specialized chemical reaction depictions for catalyzed reactions and differential equation interpretations of these depictions.

| Reaction Syntax | ODE interpretation |
|---|---|
| $\{S \xrightarrow{E} P, k\}$ | $S' = -k \cdot E \cdot S = -P'$ |
| $\{S \xrightarrow{E} P\}$ | $S' = \dfrac{(k + vE)S^n}{K^n + S^n} = -P'$ |

Several forms of transcriptional regulation can be represented by the left-bar arrow. Although this operator can also used for catalytic Hill functions, such operator overloading presents no confusion because the overscript is never used in the transcriptional form. The input canonical forms for transcription can preferably be:

$$\{A \mapsto B, f[options]\} \tag{28}$$

where f indicates the format of the regulatory function, and options is a list of rules that define system parameters (constants). Regulatory functions currently available are: hill (Hill functions); GRN (for *Genetic Regulatory Network*) neural-network dynamics; and NHCA (for *Non-Hierarchical Cooperative Activation* (Mjolsness, E., "Trainable gene regulation networks with applications to Drosophila pattern formation," In: Computational Models of Genetic and Biochemical Networks, ed. Bower, J. M., Bolouri, H. MIT Press (2000)) a form of pseudo-Monod-Wyman-Changeux dynamics (Shapiro, B. E, et al., In: Foundations of Systems Biology, ed. H. Kitano. MIT Press, Cambridge, Mass. (2001), incorporated by reference herein in its entirety.

A Hill function reaction of the form $$\{A \mapsto B, hill\ [vmax \to v, nhill \to n, khalf \to K, basalRate \to \{r_0, r_1\}]\} \tag{29}$$

can be interpreted as the differential equation $$B' = r_0 + \frac{r_1 + vA^n}{K^n + A^n} \tag{30}$$

The concentration of species A is not affected by the reaction. If a set of p reactions of the form $$\{\{A_1 \mapsto B, hill[\ldots]\}, \ldots, \{A_p \mapsto B, hill[\ldots]\}\} \tag{31}$$

where the hill options have been suppressed for clarity, the differential equation becomes $$B' = r_0 + \frac{\left(r_1 + \sum_{i=1}^{p} v_i A_i\right)^n}{K^n + \left(r_1 + \sum_{i=1}^{p} v_i A_i\right)^n} \tag{32}$$

The set of parameters $v_i$ are the connection strengths for the corresponding neural network.

A reaction involved in a genetic regulatory network of the form:

$$\{A \mapsto B, GRN[RGRN \to R, TGRN \to T, nGRN \to n, hGRN \to h]\} \tag{33}$$

is interpreted as the differential equation $$B' = \frac{R}{1 + e^{-TA^n + h}} \tag{34}$$

Here T is the connection strength and h is the activation threshold. The concentration of species A is not affected by the reaction. If we have a set of p reactions of the form $$\{\{A_1 \mapsto B, GRN[\ldots]\}, \ldots, \{A_p \mapsto B, GRN[\ldots]\}\} \tag{35}$$

the differential equation becomes $$B' = R\left[1 + \exp\left(-\sum_{i=1}^{p} T_i A_i^{n_i} + h_i\right)\right]^{-1} \tag{36}$$

where the $T_i$ and the $h_i$ are the connection strengths and thresholds for activation of B by $A_i$.

A non-hierarchical cooperative activation type of regulation provides a non-hierarchical reduction of the HCA (hierarchical cooperative activation, (Mjolsness, E. (2000)) algorithm that has been previously proposed. A reaction of the form $$\{A \mapsto B, NHCA[TPLUS \to T^+, TMINUS \to T^-, nNHCA \to n, kNHCA \to k, mNHCA \to M]\} \tag{37}$$

is interpreted as the differential equation $$B' = \frac{(1 + T^+ A^n)^m}{k(1 + T^- A^n)^m + (1 + T^+ A^n)^m} \tag{38}$$

where the $T^+, T^-$ are the connection strengths for activation and inhibition. The plus (+) and minus (−) superscripts can be replaced by specifying variable names such as TP or TM (or values) instead. Superscripts are used here to clarify the notation. Elsewhere in this paper the same options exist for the (*) superscript and the various subscripts used on variables. The subscripts could actually be indicated with a square bracket notation, e.g. $A_3[t]$ would be written as A[3][t].

Alternatively, the option TNHCA→T supercedes the TPLUS and TMINUS options, $$B' = \frac{(1 + T\Theta(T)A^n)^m}{k(1 - T\Theta(-T)A^n)^m + (1 + T\Theta(T)A^n)^m} \tag{39}$$

where $\Theta(x)$ is the Heaviside step function (see equation (109), below). With a set of p reactions of the form $$\{\{A_1 \mapsto B, NHCA[\ldots]\}, \ldots, \{A_p \mapsto B, NHCA[\ldots]\}\} \tag{40}$$

the differential equations (38) and (39) become $$B' = \frac{\prod_{i=1}^{p}(1 + T_i^+ A_i^{n_i})^m}{k\prod_{i=1}^{p}(1 + T_i^- A_i^{n_i})^m + \prod_{i=1}^{p}(1 + T_i^+ A_i^{n_i})^m} \tag{41}$$

and $$B' = \frac{\prod_{i=1}^{p}(1+T_i\Theta(T_i)A_i^{n_i})^m}{k\prod_{i=1}^{p}(1-T_i\Theta(-T_i)A_i^{n_i})^m + \prod_{i=1}^{p}(1+T_i\Theta(T_i)A_i^{n_i})^m} \quad (42)$$

respectively. If competitive binding is allowed the syntax $$\{<A_1,A_2,\ldots,A_p>\mapsto B, \text{NCHA[TPLUS}\rightarrow\{T_1^+, T_2^+,\ldots\},\ldots]\} \quad (43)$$

can be used, where the NHCA options are specified as lists but are otherwise identical to (28). The corresponding differential equations are $$B' = \frac{1+\left(\sum_{i=1}^{p} T_i^- A_i^{n_i}\right)^m}{k\left(\sum_{i=1}^{p} T_i^- A_i^{n_i}\right)^m + \left(\sum_{i=1}^{p} T_i^+ A_i^{n_i}\right)^m} \quad (44)$$

and $$B' = \frac{1+\left(\sum_{i=1}^{p} T_i\Theta(T_i)A_i^{n_i}\right)^m}{k\left(\sum_{i=1}^{p}(-T_i)\Theta(-T_i)A_i^{n_i}\right)^m + \left(\sum_{i=1}^{p} T_i\Theta(T_i)A_i^{n_i}\right)^m} \quad (45)$$

respectively. Because the methods of the present invention typically automatically generate all of the terms in all of the necessary differential equations no additional constraints are needed to force mass conservation. However, this will sometimes lead to the generation of redundant reactions, which the user may want to suppress. For example, suppose that A can exist in either of two forms, A and A*, where the total mass of $A+A^*=A_T$ is a constant, but that only the activated form A* can be converted into B. Biochemically we could input the reactions $$A \xrightarrow{k1} A^*, A^* \xrightarrow{k2} B, A+A^* = A_T \quad (46)$$

as:

$$\text{interpret}[\{\{A\rightarrow AS,k1\},\{AS\rightarrow B,k2\}\}] \quad (47)$$

The interpret function would return the following differential equations:

$$\{A'[t]=-k1A[t], AS'[t]=k1A[t]-k2AS[t], B'[t]=k2AS[t]\} \quad (48)$$

If the specific concentration of AS is not of interest, for example if it is not used elsewhere in the reaction schema, then we can use the "complement" notation $$\text{interpret}[\{\{\text{Comp}[A,AT]\rightarrow B,k2\}\}] \quad (49)$$

which produces the single differential equation $$B'[t]=k2(AT-A[t]) \quad (50)$$

The complement notation can be used for any reaction; the default total concentration is 1.

The following section describes how hierarchical canonical forms can be utilized by preferred embodiments of the methods of the present invention to transform biochemical representations of biological networks to mathematical representations. In standard biochemical notation, protein cascades are represented by a arrow-sequence of the form $$A \Rightarrow B \Rightarrow \quad (51)$$

where each step (the A, B, . . . ) would represent, for example, the activation of a particular molecular species. The methods and systems of the present invention translate the cascade (17) into a computable form while retaining the biological notation in the user interface. Mathematically, we can specify such as cascade as a multiset $$C=\{P,R,IC,I,F\} \quad (52)$$

where P is a set of proteins, R is a set of reactions, IC is a set of initial conditions, I is a set of input functions, and F is a set of output functions.

To illustrate this transformation process (from the biochemical notation, such as in equation (51), to the mathematical notation, as in equation (52)), we consider the example where equation (51) represents a simple linear phosphorylation cascade. In this case equation (51) would mean that A facilitates the phosphorylation of B, which in turn facilitates the phosphorylation of C, and so forth. In general, a cascade can have any length, so we define the elements of a cascade with a simple indexed notation, e.g., $$K_4 \Rightarrow K_3 \Rightarrow K_2 \Rightarrow K_1 \quad (53)$$

where K is used to indicate that all the members of the cascade induce phosphorylation of their substrates, that is they are kinases. In general, activation can proceed by any specified means.

This indexed notation is always used internally by the program. The user, however, has the option of using either common names or the indexed variables. There is still a great deal of information hidden in this expression, such as how many phosphate groups must be added to make each successive protein active. In the MAPK cascade for example (as explained below), the input signal that starts this cascade is $K_4$. The output, however, is not $K_1$, as this notation would suggest, but a doubly phosphorylated version of $K_1$. Hence for MAPK cascade we introduce a modified notation:

$$K_3 \xrightarrow{K_4} $$
$$K_2 \xrightarrow{K_3^*} K_2^* \xrightarrow{K_3^*} *$$
$$K_1 \xrightarrow{K_2^{**}} K_1^* \xrightarrow{K_2^{**}} * \quad (54)$$

where each phosphate group that has been added is indicated with an asterisk. From this notation it is clear that the input is $K_4$ and the output is $K_1^{**}$.

In general, suppose we have a cascade formed by n proteins $K_1, K_2, \ldots K_n$, and that the $i^{th}$ protein $K_i$ can be phosphorylated $a_i$ times. Denote by $K_i^j$ the fact that kinase $K_i$ has be phosphorylated j (possibly zero) times. The set P of all kinases $K_i^j$ in an n-component cascade is then $$P=\{K_i^j|i=1,2,\ldots,n, j=0,1,\ldots, \quad (55)$$

The reactions in the cascade are of the form $$R = \left\{ K_i^j \xrightarrow{K_{i+1}^{a_{i+1}}} K_i^{j+1} \middle| i=1,\cdots,n-1, j=0,\cdots,a_j \right\} \quad (56)$$

We note at this point that this notation describes a linear cascade, in which each element $K_i$ is only phosphorylated by the active form of $K_{i+1}$. It does not include other reactions, when, for example, $K_3$ might, under special circumstances, phosphorylate $K_1$ directly without the intermediate step of first phosphorylating $K_2$. Such additional reactions could be added, but they have been omitted from this presentation to simplify the discussion. We can also add the dephosphorylation enzymes, or phosphatases, with a double-arrow notation:

$$R = \left\{ K_i^j \underset{Ph_i}{\overset{K_{i+1}^{a_i+1}}{\Longleftrightarrow}} K_i^{j+1} \;\middle|\; i=1,\cdots,n-1,\; j=0,\cdots,a_j-1 \right\} \quad (57)$$

In general, it is not necessary to specify explicit conservation laws with this notation because they are built directly into the equations. For example, we do not have to separately specify that the quantities $$K_i^{Total} = \sum_{j=0}^{a_i} K_i^j \quad (58)$$

because this is implicit in the differential equations that are built using this notations. We do, however, have to specify the initial conditions, $$IC = \{K_i^j(0) | i=1,2,\cdots,n, j=0,1,\ldots,a_i\} \quad (59)$$

Next, we need to specify how the cascade is initiated. For example if $K_4$ is not present until some time $t_{on}$ and then is fixed at a level c, would write the set of input functions as $$I = \{K_4(t) = cH(t-t_{on})\} \quad (60)$$

where H(t)=0, t≤0 and H(t)=1, t>0 is the Heaviside step function. In some cases, we are only interested in the total quantity of each substance produced as a function of time, e.g., $K_i^j(t)$. More generally, we would also specify a set of output functions F. For example we might have F={f, g} where $f(T)$ is the total accumulated protein concentration after some time T, $$f(T) = \int_{t_{on}}^{T} K_l^{a_1}(t) dt \quad (61)$$

and g(c) is the steady state concentration of activated kinase, $$g(c) = \lim_{t_{on} \to \infty} \left[ \lim_{t \to \infty} K_1^{a_1}(t) \right] \quad (62)$$

where c is the input signal specified I. Then the cascade is then completely specified by the multiset C={P,R,IC,I,F}.

If we have an additional regulatory protein, such as a scaffold that holds the various proteins in equation (54) together there are additional reactions. These describe binding of the enzymes to the scaffold and phosphorylation within the scaffold. We describe the scaffold itself by defining an object $s_{P1,P2,\ldots,Pn}$ where n is as before (the number of kinases that bind to the scaffold, or alternatively, the number of "slots" in the scaffold) and $p_i \in \{\epsilon,0,1,\ldots,a_i\}$ indicates the state of phosphorylation of the proteins in each slot. Thus if $p_i = \epsilon$ (or, alternatively, −1) the slot for $K_i$ is empty, if $p_i = 0$, $K_i^0$ is in the slot, etc. For a three-slot scaffold, for example, we would add to the set P the following set $$P' = \{S_{ijk} | i = \epsilon, 0, 1, \ldots, a_2, j = \epsilon, 0, 1, \ldots, a_2, \\ k = \epsilon, 0, 1, \ldots, a_3\} \quad (63)$$

To describe binding to the scaffold, we would also add to the set R the following reactions $$R' = \{S_{p_1,\ldots,p_i=\epsilon,\ldots,\epsilon,\ldots,p_n} + K_i^j z, 27\; Sp_1, \ldots, \\ p_i = j, \ldots, p_n\} \quad (64)$$

where the indices run over all values in the range $$p_i = \begin{cases} \epsilon, 0, 1, \cdots, a_i, i \neq j \\ 0, 1, \cdots, a_i, i = j \end{cases} \quad (65)$$

For the three-member scaffold this would be $$R' = \{S_{\epsilon jk} + K_1^i \leftrightarrow S_{ijk}, i = 0, \quad (66) \\ \cdots, a_1, j = \epsilon, 0, \cdots, a_2, k = \epsilon, 0, \cdots, a_3\}$$

$$\bigcup \{S_{i\epsilon k} + K_2^j \leftrightarrow S_{ijk}, i = \epsilon, 0, \cdots, a_1, \\ j = 0, \cdots, a_2, k = \epsilon, 0, \cdots, a_3\}$$

$$\bigcup \{S_{ij\epsilon} + K_3^k \leftrightarrow S_{ijk}, i = \epsilon, 0, \cdots, a_1, j = \epsilon, \\ 0, \cdots, a_2, k = 0, \cdots, a_3\}$$

Finally, we have phosphorylation in the scaffold. This can be done either by a protein that is not bound to the scaffold, e.g., for the input signal, $$R'' = \{Sp1, \ldots, pi-1 = j < a_{i-1}, pi = ai, \ldots, pn + \\ K \Longleftrightarrow Sp1, \ldots, pi-1 = j+1, pi = ai, \ldots, pn\} \quad (67)$$

where the two-sided double arrow ($\Longleftrightarrow$) is used as shorthand for the (possibly bi-directional) enzymatic reaction, or by one that is bound to the scaffold, $$R''' = \{Sp1, \ldots, pi-1 = j < a_{i-1}, pi = ai, \ldots, \\ pn \to Sp1, \ldots, pi-1 = j+1, pi = ai, \ldots, pn\} \quad (68)$$

or by some combination of the two, all of which must be added to the reaction list R. For the three-slot scaffold with external signal $K_4$ that activates $K_3$, we have $$R'' = \{S_{i,a_2,k} \to S_{i+1,a_2,k}, i = 0, \cdots, a_1 - 1, k = \epsilon, 0, \cdots, a_3\} \quad (69)$$

$$\bigcup \{S_{i,j,a_3} \to S_{i,j+1}, a_3, i = \epsilon, 0, \cdots, a_1, j = \epsilon, 0, \cdots, a_2 - 1\} \text{ and}$$

$$R''' = \left\{ S_{ijk} \underset{Ph_3}{\overset{K_4}{\Longleftrightarrow}} S_{i,j,k+1}, i = \epsilon, 0, \cdots, \right. \quad (70) \\ \left. a_1, j = \epsilon, 0, \cdots, a_2, k = 0, \cdots, a_3 - 1 \right\}$$

Typical $a_i$ values for this type of cascade are $a_1 = a_2 = 2$ and $a_3 = 1$.

As an example, let us continue with the above-mentioned three-member cascade that is initiated with $K_4$. In what follows, and throughout this specification, we refer to Cellerator™, a Mathematical® package that implements the above algorithms. The source code of Cellerator™ is found on the compact disk filed with this specification. One of ordinary skill in the art will recognize that other programs that implement the above algorithms, or other embodiments of the methods of the present invention, can be developed using the general teachings of this specification and program development tools known in the art, especially programming tools targeted to mathematical models, especially models involving differential equations, as described above.

In Cellerator™ we have defined the function genReacts{kinase-name, n, {$a_i$}, phosphatase-name}, where kinase-name and phosphatase-name are the names we want to give to the sequences of kinases and phosphatases, respectively, and n and $a_i$ are as before. The command illustrated in FIG. 12 is provided by Cellerator™ for performing the methods of the present invention to generate the above set of reactions (54).

The input is in the first line while the output is the second line. Alternatively, the user could specify the set of reactions explicitly, or copy the output to a later cell to manually add additional reactions. If RAF has been set up as an alias for $K_3$ then the rate constants are specified by a content-addressable syntax, e.g., as illustrated in FIG. 13, corresponding to

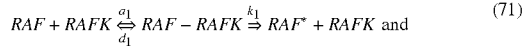  (71)

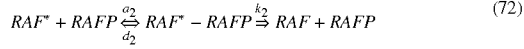  (72)

and so forth, where the numbers over the arrows indicate the rate constants (and not enzymes, as with the double arrow notation). Cellerator™ first translates the five high-order reactions (equation 54) into the corresponding set of 30 low-level reactions. Each low-level reaction (such as intermediate compound formation) is determined by applying the appropriate enzyme-kinetics description, and has a unique rate constant. The low-level reactions are subsequently translated into the appropriate set of 21 differential equations for the eight kinases, three phosphatases and ten intermediate compounds. When scaffold proteins are included (discussed below) these numbers increase to 139 high level reactions, 348 low-level reactions (300 without kinases), and 101 differential equations (85 without kinases).

As another illustration of an implementation of the use of canonical forms to represent biological networks according to preferred embodiments of the methods of the present invention, consider the glycolytic step in which an activated form of the enzyme phosphofructokinase (PFKA) catalyzes the phosphorylation of fructose 6-phosphate (F6P), converting ATP to ADP in the process, $$F6P+PFKA+ATP \rightleftharpoons X \rightarrow F6P^*+PFKA+ADP \quad (73)$$

where X is a sequence of intermediate compounds that are formed during the process. In a reduced model of glycolysis (Goldbeter, A., and Lefever, R., *Biophys J.* 12:1302-1315 (1972)). PFK catalyzes the removal of a phosphate from ATP,

  (74)

where Y is the intermediate compound formed by PFKA and ATP, and $k_1$, $k_{-1}$ and $k_2$ are rate constants. The specialized chemical reaction depiction for (74) can be

  (75)

To include the rate constants (75) could be replaced with

  (76)

Omitted rate constants can take on default values. In addition ADP also activates PFK, ATP is continually produced, and ADP is continually degraded. In chemical notation,

  (79)

The canonical form for conversion of A to B can be A→B. To describe (77) and (78), preferred embodiments of the methods of the present invention such as Cellerator™ use the special symbol Ø to indicate conversion to (annihilation) or from (creation) the empty set. A bi-directional arrow (⇅) can indicate that the reaction can proceed in both ways, as in equation (79).

The reactions, once expressed in canonical form, can then be translated to differential equations according to the law of mass action using the rules described above for interpretation of canonical input forms of chemical reactions as differential equations. This interpretation can be initiated by a user for example, by calling an interpret function that is programmed to perform the rules described above. The complete set of canonical forms for the simplified glycolytic model, along with the corresponding set of automatically generated differential equations, is illustrated in FIG. 3. When the same chemical species X occurs in multiple reactions, one term (or set of terms) can be generated in the differential equation for X'(t) for each reaction. The final interpreted differential equation then gives the sum of all these reaction terms (see, for example, the differential equation for ADP in FIG. 3.

The methods of the present invention can be used to study biological networks that are important for the development of an organism. For example, by extending the standard signal transduction network hierarchy so that nodes represent cells rather than chemical concentrations we can describe multi-cellular systems such as plant shoot apical meristems (SAMs). Links then refer to intercellular—rather than intermolecular—interactions. The essential physiology of many developmental processes can be captured by only a small number of cells. Thus, the complexity of multi-cellular networks arises from the number of interactions rather than the number of nodes. This is because many different mutually interacting signal transduction networks need to be represented within each cell. There will be many instantiations of essentially the same network (e.g., mitotic oscillators) in each cell, or even multiple instantiations of the same network (e.g., MAP-kinase cascades or transcription complexes) within a single cell. The 215-cell SAM illustrated in FIG. 4, for example, has 976 near-neighbor links (out of a possible 215×214=46,010 cell-cell links). Using the minimal developmental system presented below, this SAM is described by 1690 ODEs. Birth and death processes change the total number of cells—and hence the total number of differential equations required to describe the system—and thus pose an even more difficult problem. These must be dealt with as a time-dependent variable structure system (VSS).

The paradigm of organisms-as-graphs can represent many of the basic features of developing tissue. Furthermore, the methods of the present invention can be extended to utilize a variable-structure graph-based algorithm to describe simple developmental processes. In particular, a VSS can be implemented using a pre-packaged fixed-structure differential equation solver, according to the methods of the present invention, as described in further detail hereinbelow.

An automated method for simulating a developmental process of an organism according to the present invention can include the following steps:

a) receiving initial condition values and process parameters for the developmental process of the organism;

b) representing the organism or a tissue within the organism by a graph data structure, wherein the graph data structure includes:

i) a list of links, each link representing the interaction between two cells;

ii) a lineage tree recording the family tree of cell birth for the cells represented by the list of links; and iii) a list of nodes, each node representing a cell of the cells represented by the list of links, with an embedding describing the location of the cell in Cartesian coordinates and a set of differential equations describing the time evolution of the location of the cell, the differential equations including the initial condition values and process parameters, each node having a model that includes a system of differential equations and associated parameters describing the developmental process; and c) repeatedly solving the set of differential equations in a series of steps for a defined number of steps, wherein after each step results are generated and compared to a threshold to determine whether the developmental process has reached a trigger point for changing the number of nodes in the list of nodes, thereby simulating the developmental process.

The method can preferably include:

d) graphing the nodes using the Cartesian coordinates.

The developmental process can be, for example, cell division, wherein reaching the trigger point adds a new node to the list of nodes.

The developmental process can be, for example, cell death, wherein reaching the trigger point removes node from the list of nodes. The initial condition values and process parameters are typically input by a user before being received by a computer system performing a method according to the present invention.

To provide an object-oriented representation of organisms-as-graphs we have developed the concepts of domain and field. A domain, in analogy with the standard use of the term in mathematics, is an object-oriented representation of the mathematical domains that are relevant to solving a particular scientific problem. A field is a representation of a function that maps domains to the real numbers. We instantiate a domain by applying the expand function to it.

For example, we can define the integer domains $I(n)$, $I(m,n)$, and $I(m,n,p)$ to represent the sets $\{1,2,\ldots,n\}$, $\{m,m+1,\ldots,n\}$, and $\{m,m+p,m+2p,\ldots,m+qp\}$, where q is the largest integer such that $m+qp \leq n$, respectively. Then the expand function, which we will denote by E herein, maps the object representation of the domain to an implementation of that domain, e.g., $$E[I(n)] = \{1,2,\ldots,n\}$$

$$E[I(m,n)] = \{m, m+1, m+2, \ldots, n\}$$

$$E[I(m,n,p)] = \{m, m+p, m+2p, \ldots, m+qp\} \quad (80)$$

Thus the expand function applies the implementation. In actual practice we would generally never have to deal with the expanded function itself. To see what a field is, suppose g is any function that operates on the integers. Then the field operator, which we will denote by F herein, $$F: D \rightarrow D \times R \quad (81)$$

associated with any function $f(x): D \rightarrow R$ (here R denotes the real numbers) generates a set of ordered pairs $$F(f,D) = \{(d_i, f(d_i, f(d_i))) | d_i \in D\} \quad (82)$$

We will use the shorthand $f(D)$ for the set $$f(D) = \{f_i | (d_i, f_i) \in F(f,D), d_i \in D\} = \{f(d_i) | d_i \in D\} \quad (83)$$

which we will call the range of the field corresponding to $f$.

To illustrate the concept of fields, suppose that $D = I(5, 19, 3)$ and that $f(x) = x^2$. Then $$E[D] = \{5, 8, 11, 14, 17\} \quad (84)$$

and $$F[f,D] = \{(5,25), (8,64), (11,111), (14,196), (17,289)\} \quad (85)$$

$$f[D] = \{25, 64, 111, 196, 289\} \quad (86)$$

Using fields one can also define composite functions that map domains to the real numbers. For example, let $A \subset \mathcal{R}$ and $f: \mathcal{R} \rightarrow \mathcal{R}$ be a function. Then we define the sum function $\Sigma(f,A): S[\mathcal{R}] \rightarrow \mathcal{R}$ (where s[U] is the subset operator that gives the set of all subsets of the set U)

$$\Sigma(f,A) = \Sigma_{x \in A} f(x) \quad (87)$$

The sum function applies $f$ to every element of A and then sums the result; equation (86) might be read as "the sum of j(x) over the set A." If D is a domain and we let $A = E[D]$ we can define the sum operator–which gives the sum of the function $f(x)$ over a domain D—as $$\Sigma_D f(x) \equiv \Sigma(f, E[D]) = \Sigma_{x \in E(D)} f(x) = \Sigma_{y \in f(D)} y \quad (88)$$

For example, letting g be the identity function ($g(x)=x$), $$\sum_{I(10)} g(x) = \sum_{k=1}^{10} k = 55 \quad (89)$$

We next define a field of domains as a function that maps domain elements to domains. Generalizing equation (81), let A be a set of domains $$A = \{D_1, D_2, \ldots\} \quad (89)$$

and let $F: D \rightarrow A$ be a function that maps domain elements to domains. Then we define the field of domains $F: D \rightarrow D \times A$ associated with F as the set of ordered pairs $$F(F,D)=\{(d_i,F(D))|d_i\epsilon D\} \quad (90)$$

and write $$F(D)=\{f(d_i)|d_i\epsilon D\} \quad (91)$$

for the range of the field of domains corresponding to F.

Fields of domains are particularly useful because they can be defined dynamically. In a developmental simulation, for example, domains can be used to represent sets of cells. We will then often need to answer the following question: given any cell in an organism, what other cells interact with it? We can define a domain T (for "Tissue") to represent a collection of cells, possibly an entire organism, and let A=S[T]={$T_1$, $T_2$, . . . } be the set of domains generated by considering all possible combinations of cells in T. Then the elements t∈T represent cells of T. Each t has associated with it a set of other cells Nbr[t]≡{$t_1$∈T|t,$t_i$ are neighbor}∈A. The mapping N:t∈T→Nbr[t]∈A gives us a neighborhood function that tells us which cells are neighbors of other cells. The corresponding field of domains N:T→T×A formally defines this as the set of ordered pairs N [t]={(t,N(t))|t∈T}, or more concisely, the range of N is expressed as N(T)={N(t)|t∈T}. It is possible to implement the neighborhood field of domains via a potential function operator v($t_i$,$t_j$) that is nonzero only when there is some interaction between the two cells. We want N [t] to give us the ordered pair (t,N[t]), where $$N[t]=\{t_j\epsilon T|V(t,t_j)\neq 0\} \quad (92)$$

We can now proceed to define dynamic operators. Let g:{E[$T_i$]}→R be a function. Then by generalizing our sum function (see equation 49), we can calculate a sum over neighbors operator $\Sigma_N$ g as $$\Sigma_{N[t]}g[t]=\Sigma(g,E[N[t]])=\Sigma_{n\epsilon N[t]}g(n) \quad (93)$$

to give the sum over all neighbors of t of the function g. To illustrate the sum over neighbors, suppose that ψ(t,u) is the electrostatic potential between cells t and u. The total electrostatic $\omega_T$(t) potential at t is $$\omega_T(t)=\Sigma_{u\epsilon N[t]}\psi(t,u) \quad (94)$$

where N picks out those neighbors u of t that are not electrically shielded from t.

Domains can be implemented, for example, with uninstantiated Mathematica® functions; the expand function is perform using up-values, e.g., the integer domain I(m,n) is defined as $$\text{expand}[\text{intDomain}[m\_,n\_]]\hat{}:=\text{Range }[m,n] \quad (95)$$

with similar definitions for the other domains. The notations of pure function, Apply, and Map very nicely fit into the concept of fields and operators on domains. However, this formal presentation gives us a mechanism whereby domains and fields could be implemented with any computer language, freeing us from the specifics of Mathematica®.

Figure 4:
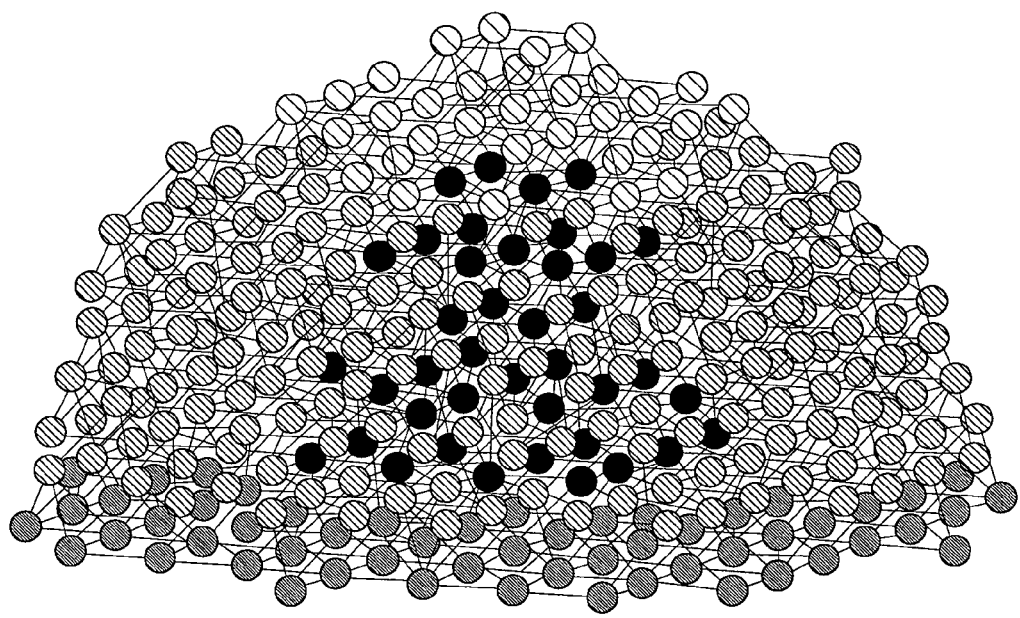
FIG. 4 illustrates the initial conditions for a 215 cell shoot apical meristem (SAM) simulation. Node shades indicate cell type.
Figure 5:
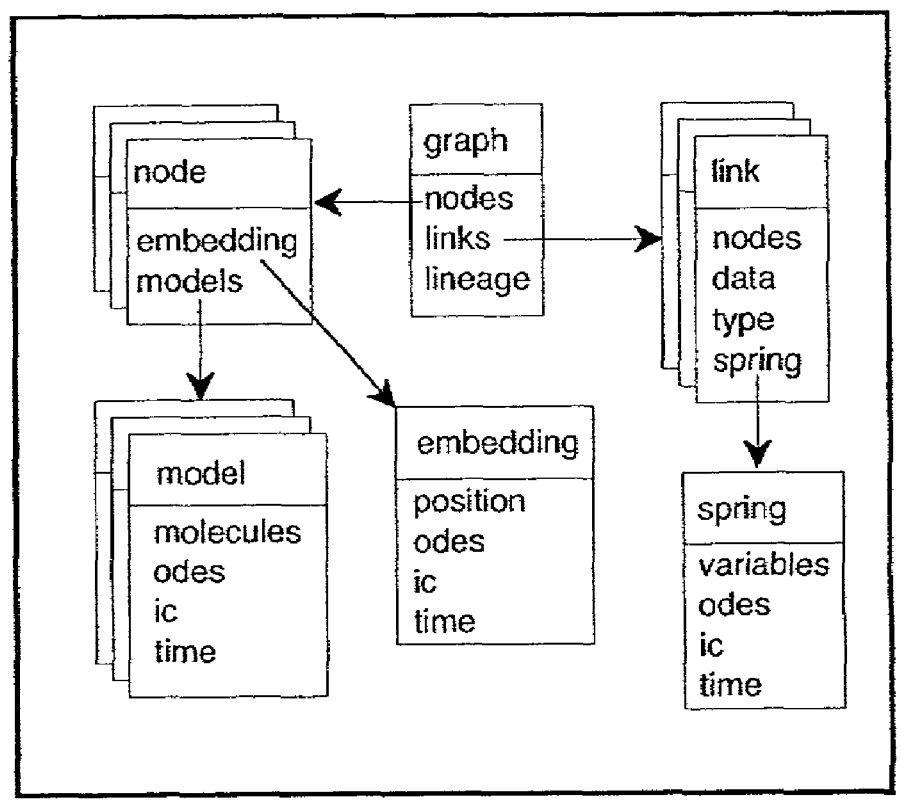
FIG. 5 is a diagram of the structure of graph domains.

In another aspect, the present invention provides an organism-as-graph approach to simulate a growing organism. For this approach a growing organism (or more likely, selected tissue within a growing organism) is represented by a graph data structure. In one preferred embodiment, a graph is composed of three things: a list of nodes, a list of links, and a lineage tree. Each node represents a particular cell; each link represents the interaction between two cells; and the lineage tree records the family tree of cell birth. The overall object hierarchy is illustrated in FIG. 5. The shoot apical meristem illustrated in FIG. 4 gives an example of the spatial orientation of the physical graph represented by this data structure.

For example, a graph domain according to preferred embodiments of the present invention, can be represented as $$g=\text{graphDomain}[\text{nodes}\to\{n1,n2,\ldots\},\text{links}\to\{l1, l2,\ldots\},\text{lineage}\to T \quad (96)$$

Each node contains precisely one embedding and one or more models, $$n1=\text{nodeDomain}[\text{embedding}\to e1\text{ models}\to\{m1,m2\}] \quad (97)$$

The embedding describes the location of the cell in Cartesian coordinates, and an optional set of differential equations (and corresponding initial conditions) that describe the time evolution of those coordinates. In the simplest implementation only a single point is needed to describe a node's embedding; however, there is no reason that additional information, such as the shape of a cell and its geometric relationship to other cells, could not be included.

$$e1=\text{embeddingDomain}[\text{position}\to\{x1,y1,z1\}, \text{nodes}\to\{x1'==f1[x1,y1,z1],\}\text{ic}\to\{x10, y10,\ldots\},\text{time}\to t0] \quad (98)$$

The time indicates when the initial conditions are applied.

Each node can contain one or more models. Each model domain contains a system of differential equations and associated parameters that describe some aspect of that cell's signal transduction network. In theory, one could put all of the differential equations for a cell in a single model. In preferred embodiments, however, different models are generated for distinct parts of the network. The differential equations in one model can refer to variables in another model (in fact, they can refer to variables in another node, as well). For example, to describe cell division it might be convenient to group the equations into separate models representing the G1 checkpoint, the G2 checkpoint, DNA replication, Mitosis, etc. For example, if we want the glycolytic system r illustrated in FIG. 3, all that is necessary to specify is $$\{\text{eqns,vars}\}=\text{interpret}\{r\};\text{ m=modelDomain} [\text{molecules}\to\text{vars, nodes}\to\text{eqns}]; \quad (99)$$

Options that are not specified take on default values; for example, unspecified initial conditions and the initial time are set to zero. If a number of nodes $n_1$, . . . ,$n_k$ were present, each of which required a glycolytic system, indices could be added to the variables, i.e., ADP becomes ADP [i], i=1, . . . ,k. One of ordinary skill in the art recognizes that this process is easily automated.

Figure 6:
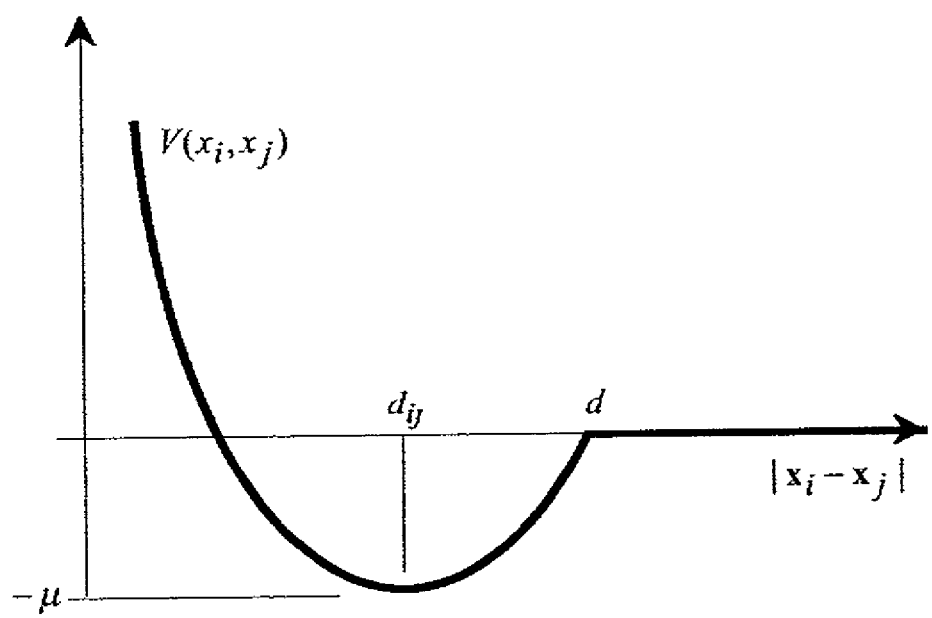
FIG. 6 graphically illustrates "spring" potential (see equation 65).

The minimum information contained in a link is a reference to two nodes, such as. l1=linkDomain[nodes→{i,j}]. In preferred embodiments each node is numbered as it is added to the graph, so the nodes are represented by those integers. Pointers could also be used. Additional information about the link can also be placed in the data field. Each link may also contain an associated "spring" field that represents the dynamics of cell growth. These springs are used to define a potential function (FIG. 6) that is used to optimize the position of the nodes after each growth step. The potential function for a node $n_i$ is $$V_{ij}=\frac{1}{2}\sum_j k_{ij}(|x_i-x_j|-d_{ij})^2 \quad (100)$$

where the sum is taken over all nodes $n_j$ that are linked to $n_i$, $x_i$ are the vector positions of the nodes, the $k_{ij}$ are interaction strengths (zero for non-interacting nodes), and the $d_{ij}$ give the desired distance between the nodes. The potential gets "turned off" when the interaction distance becomes too large in some sense; to prevent a discontinuity in the potential after cell division we modify (100) as:

$$V_{ij} = \frac{1}{2}\sum_j k_{ij} c_{ij}[(|x_i - x_j| - d_{ij})^2 - \mu] \quad (101)$$

where $$c_{ij} = \begin{cases} 1, & d_{ij} \leq d \\ 0, & d_{ij} > d \end{cases} \quad (102)$$

The biological dynamics of growth are then described by assigning a relationship between $d_{ij}$ and the model variables in nodes $n_i$ and $n_j$. For example, suppose that the model stipulates that a cell's mass grows at a constant rate, $$\frac{dM_i}{dt} = kM_i (M_i = M_{i0} e^{kt}) \quad (103)$$

and that we describe the cell as a sphere of radius $R_i$. Then if the density remains constant, $$\frac{dR_i}{dt} = \frac{1}{3}kR_i (R_i = R_{i0} e^{kt/3}) \quad (104)$$

then we might constrain the equilibrium spring distance to be $$d_{ij} = R_i + R_j \quad (105)$$

if the cells are assumed to be touching. After each step, the potential is then minimized (e.g., via gradient descent or simulated annealing) to determine the new position of the cell. For a small number of nodes the optimization can be replaced by adding an additional differential equations of the form $$\frac{dx_i}{dt} = -\nabla V_{ij} \quad (106)$$

This forces the solution to follow a gradient descent towards the minimum of the spring function. As a final note, the term "spring" here is used because of the form of the potential function, and does not actually describe position dynamics (otherwise, equation 106 would be second order in time). In fact, equation 106 gives an exponential relaxation towards local minimum, akin to the motion of a spring in a highly viscous medium.

The methods of the present invention can be used to simulate variable structure systems. Biologically, the birth of new cells and the death of old cells occur as a result of the concentration of some chemical species passing a species. For example, the amount of ATP can fall so low that metabolic processes cease (death) or the quantity of S-phase promoting factor (SPF) may increase so high that DNA replication is induced (birth). In the first case, the number of active cells in the system ceases to exist; in the second case, an additional cell is added.

It is easier to represent death than birth. We can assign an indicator, or "aliveness," variable $I_k$ to each cell k, where $I_k = 1$ if cell k is alive, and $I_k = 0$ if cell k dies. Then if we multiply the concentration of each chemical species x in cell k by $I_k$, all equations for a given cell effectively disappear when the cell dies. In principle we could do the same thing to describe birth. However, this would require that we know in advance the total maximum number of cells we would ever want to simulate. We would never be allowed to exceed this number. Besides its inelegance such an algorithm could be a computationally very expensive. Thus we propose an alternative mechanism to represent cell birth.

We assume that any change in the size of the system (i.e., the number of variables and differential equations and/or the values of corresponding initial conditions) is triggered by some threshold passage. Suppose that our system is composed of M+N variables, $\{x_i\}_{i=1,\ldots,N}$ and $\{w_i\}_{i=1,\ldots,M}$, where each of the N variables $x_i$ can trigger some event when it passes a corresponding threshold $T_i$, and there are M remaining variables $w_i$ in the total system. Then we define a set of flag variables $\{y_i, z_i\}_{i=1,\ldots,N}$, where there is one pair of flag variables for each trigger variable $x_i$. Then if the event is triggered the first time that $x_i > T_i$ we force the corresponding flag variables to satisfy the ODEs $$\frac{dy_i}{dt} = \Theta(x_i - T_i), \; y_i(0) = 0 \quad (107)$$

$$\frac{dz_i}{dt} = \Theta(y_i), \; z_i(0) = 0 \quad (108)$$

where $\Theta(x)$ is the unit step function $$\Theta(x) = \begin{cases} 0, & x < 0 \\ 1, & x \geq 0 \end{cases} \quad (109)$$

A similar equation can be written if the event is triggered by $x_i < T_i$. Then $y_i$ increases linearly from zero whenever $x_i$ is above threshold. Even if $x_i$ falls back below threshold, $y_i$ will remain positive; it stays fixed at whatever value it had when $x_i$ falls back below threshold. The second new variable $z_i$ increases linearly with time whenever $y_1$ is positive. Thus $z_i$ measures the total amount of time that has elapsed since $x_i$ first passed its threshold.

These new variables are then used as follows. We submit our entire system $\{x_i, y_i, z_i\}_{i=1,\ldots,N} \cap \{w_i\}_{i=1,\ldots,M}$ to a fixed-structure solver for some time interval of length T. Here T is the total duration of numerical integration, and is not the integration step size, which is typically (several) orders of magnitude smaller. We chose T to have a magnitude close to the expected time between triggering events (e.g., the length of the cell cycle). Presumably the solver will return the solutions to the differential equations (in the form of interpolatable functions of some sort) over the time interval (0,T). Then we evaluate each of the variables $z_i$ at the end of the solution interval (time t=T). If $z_i(T) = 0$ $\forall i = 1, \ldots, N$ then no even occurred. Otherwise some event has occurred. Since it is possible that more than one of the $z_i$ are nonzero we must examine them all to determine which one is the biologically meaningful one, i.e., which event occurred first. To determine this we calculate $$z_k = \max_{i \leq i \leq N} z_i \qquad (110)$$

Then $x_k$ is the first variable that passed threshold, and this event occurred at time $$t = T - z_k \qquad (111)$$

So we accept the solution provided over the interval $(0, T-z_k)$ but reject the rest of the solution, over the interval $(T-z_k, T)$. We define a new set of initial conditions at $T-z_k$ by evaluating the numerical solutions for $x_i$ and $w_i$ at that time, and setting $y_i(T-z_k)=0$ and $z_i(T-z_k)=0$. We then add whatever new variables are necessary to the system at $T-z_k$ (along with their corresponding differential equations and initial conditions). If some of these new variables can trigger events we must also add whatever new $y_i$ and $z_i$ variables are required to describe these new potential event triggers. Then we have a new system with a larger number of variables. The entire process is then repeated over the interval $(T-z_k, 2T-z_k)$ and is iterated as desired.

The following examples are intended to illustrate but not limit the invention.

EXAMPLE 1

Simulation of MAPK Pathway with Scaffolds

This example provides a method for automatic model generation of a dynamic regulatory network, the mitogen-activated protein kinase (MAPK) cascade signal transduction module operating in solution or when bound to a scaffold.

The mitogen-activated protein kinase (MAPK) cascades (FIG. 1) are a conserved feature of a variety of receptor mediated signal transduction pathways (Garrington, T. P. and Johnson, G. L., *Curr. Opin. Cell. Biol.*, 11, 211-218 (1999); Widmann, C., et al., *Physiol. Rev.* 79, 143-180 (1999); and Gustin, M. C., et al., *Microbiol. Mol. Biol. Rev.*, 62, 1264-1300 (1998)). In humans they have been implicated in transduction of signals from growth factor, insulin and cytokine receptors, T cell receptor, heterotrimeric G proteins and in response to various kinds of stress (Garrington, T. P. and Johnson, G. L., *Curr. Opin. Cell. Biol.* 11, 211-218 (1999); Putz, T., et al., *Cancer Res.* 59, 227-233 (1999); Stemberg, P. W. and Alberola-Ila, J., *Cell* 95, 447-450 (1998); Crabtree, G. R. and Clipstone, N. A., *Annu. Rev. Biochem.* 63, 1045-1083 (1994); and Kyriakis, J. M., *Biochem. Soc. Symp.* 64, 29-48 (1999)). A MAPK cascade consists of three sequentially acting kinases. The last member of the cascade, MAPK is activated by dual phosphorylation at tyrosine and threonine residues by the second member of the cascade: MAPKK. MAPKK is activated by phosphorylation at threonine and serine by the first member of the cascade: MAPKKK. Activation of MAPKKK apparently proceeds through different mechanisms in different systems. For instance, MAPKKK Raf-1 is thought to be activated by translocation to the cell membrane, where it is phosphorylated by an unknown kinase. All the reactions in the cascade occur in the cytosol with the activated MAPK translocating to the nucleus, where it may activate a battery of transcription factors by phosphorylation.

MAPK cascades have been implicated in a variety of intercellular processes including regulation of the cell cycle, apoptosis, cell growth and responses to stress. These molecules are of crucial importance in the development of memory and wound healing. Abnormal changes in MAPK pathway regulation often mediate various pathologies, most notably cancer. This central role of MAPK mediated signal transduction in most regulatory processes makes it an especially attractive research and modeling object.

Signal transduction through a MAPK cascade can be very inefficient unless additional regulatory proteins, called scaffolds, are present in the cytosol. Scaffold proteins nucleate signaling by binding two or more MAP kinases into a single multi-molecular complex. It has been reported previously that scaffolds can both increase and decrease the efficiency of signaling in a concentration dependent manner (Levchenko, A., et al., *Proc. Natl. Acad. Sci. USA*, 97(11): 5818-23 (2000), incorporated by reference herein in its entirety). In addition they can reduce the non-linear activation characteristics of the cascade. These properties may be crucial for global and local activation of MAPK as scaffold proteins may selectively translocate to small subcellular compartments, thus locally facilitating or inhibiting MAPK activation. This Example demonstrates the use of a software package called Cellerator™ to perform a method of the present invention to substantially improve earlier MAPK cascades models and study the parametric dependence of the MAPK cascade in a manner not investigated in the preceding report.

As described above, addition of scaffold proteins into the MAPK reaction system results in markedly increased number of states and equations describing transitions between them. Here the benefits provided by the methods of the present invention can be appreciated, as a simple sequence of commands can lead to automatic description of all reactions involving scaffold-kinase complexes (see FIG. 14).

In the simulation performed in this Example the first goal was to verify the automatic model generation for scaffold-mediated MAPK cascade as implemented using a method according to the present invention. As a basis for the comparison we referred to a previous report describing a quantitative model of the effect scaffold proteins can play in MAPK mediated signal transduction manner (Levchenko, A., et al., (2000), incorporated herein by reference in its entirety). The same parameter values were used for the analysis as those used in Levchenko et al. (2000) (shown in Table 4 according to the parameter designations of Levchenko et al (2000)).

TABLE 4

Parameter values used in the model (unless otherwise stated)

| Parameter | Value assumed* |
|---|---|
| Concentrations, µM | |
| [MAPKKK] | 0.3 |
| [MAPKK] | 0.2 |
| [MAPK] | 0.4 |
| [MAPKKK K-ase] | 0.2 |
| [MAPKKK P-ase] | 0.3 |
| [MAPKK P-ase] | 0.2 |
| [MAPK P-ase] | 0.3 |
| Association rate constants, $\mu M^{-1} \cdot sec^{-1}$ | |
| $a_1$ | 1 |
| $a_2$ | 0.5 |
| $a_3$ | 3.3 |
| $a_4$ | 10 |
| $a_5$ | 3.3 |
| $a_6$ | 10 |
| $a_7$ | 20 |

TABLE 4-continued

Parameter values used in the model (unless otherwise stated)

| Parameter | Value assumed* |
|---|---|
| $a_8$ | 5 |
| $a_9$ | 20 |
| $a_{10}$ | 5 |
| $on_1$ | 10 |
| $on_2$ | 10 |
| Dissociation rate constants, $sec^{-1}$ | |
| $d_1$ | 0.4 |
| $d_2$ | 0.5 |
| $d_3$ | 0.42 |
| $d_4$ | 0.8 |
| $d_5$ | 0.4 |
| $d_6$ | 0.8 |
| $d_7$ | 0.6 |
| $d_8$ | 0.4 |
| $d_9$ | 0.6 |
| $d_{10}$ | 0.4 |
| $off_1$ | 0.05 |
| $off_2$ | 0.05 |
| $off_3$ | 0.05 |
| $off_4$ | 0.5 |
| Reaction rate constants, $sec^{-1}$ | |
| $k_1$ | 0.1 |
| $k_2$ | 0.1 |
| $k_3$ | 0.1 |
| $k_4$ | 0.1 |
| $k_5$ | 0.1 |
| $k_6$ | 0.1 |
| $k_7$ | 0.1 |
| $k_8$ | 0.1 |
| $k_9$ | 0.1 |
| $k_{10}$ | 0.1 |

*The concentrations and individual a, d, and k values correspond to estimates in Ferrell, J. E., J. Trends. Biochem. Sci., 21, 460-466 (1996) and Bray, D. & Lay, S., Proc. Natl. Acad. Sci. USA 94, 13493-13498 (1997).

Additionally, all the assumptions of the model of Levchenko et al. (2000) were made for this analysis. These assumptions included 1) dephosphorylation of kinases in scaffold complexes is precluded; 1) there is no binding of partially or fully activated MAPKK or MAPK to the scaffold; the activation of MEK and MAPK when bound to a scaffold is processive rather than distributive with the reaction rate equal to the rate of a single phosphorylation reaction; 3) kinases bind to the scaffold independently of one another, i.e., there is no cooperativity in the binding; 4) scaffold molecules do not possess catalytic properties, so that the reaction rates within a scaffold complex and in solution are equal; and 5) reactions take place in a homogenous environment with no additional mechanism for compartmentalization of molecules, thus we ignored MAPK translocation to the nucleus.

A representation of the MAPK pathway was input into the Cellerator™ platform in the following manner. The following command was entered to instruct Mathematica™ to load Cellerator™ into memory:

Get [ToFileName [
{"PikachusRescue:Research", "CelleratorFiles", "cellerator.m"}]];

The following input command was entered to generate the initial set of reactions for a MAPK cascade on a Scaffold and assigned the list of reactions to the variable c:

c=MAPKCascade [
signal→RAFK,
phosphatase→{MAPKP, MEKP, RAFP},
stages→{2, 2, 1},
solutionSignalRates→{a1, d1, k1, a2, d2, k2},
solutionPhosphorylationRates→
{{a3, d3, k3, a4, d4, k4}, 8 a5, d5, k5, a6, d6, k6},
{a7, d7, k7, a8, d8, k8}, 8 a9, d9, k9, a10, d10, k10}},
scaffoldName→S,
scaffoldSignalRates→{k1a, d1a, k1},
scaffoldPhosphorylationRates→{{k7, k9a}, {k3, k5a}}]

The output including the initial set of reactions is shown in FIG. 17.

The following command was entered to generate the Differential Equations and assign the list of differential equations to the variable s:

s=interpret [c]

The output including the differential equations is shown in FIG. 18.

When the same assumptions were made as those of Levchenko et al. (2000) (described above), exactly the same solution for the three-member scaffold case was obtained using the automated methods of the present invention (FIGS. 17-18). Note that the equations for a two-member scaffold were provided in Levchenko et al. The case of a three-member scaffold is modeled similarly, with the number of equations describing scaffold complexes tripled because of increased combinatorial possibilities for complex function. This convergence of results verified the model generated by a method according to the present invention. In addition, the difficulty of manual generation of all the necessary equations, a limiting factor of the previous study, has now been removed.

We thus attempted to study a more detailed model, in which some of the previous assumptions were relaxed. The following syntax and commands provides examples of syntax and commands entered by a user to direct Cellerator™ to numerically solve the differential equations (i.e. to initiate the equation solver function of Cellerator™. Similar commands and syntax were used to generate the results provided later in this Example.

The following commands were used to assign values to the rate constants (the input parameters):

a1=1.; a2=0.5; a3=3.3; a4=10.; a5=3.3;
a6=10.; a7=20.; a8=5.; a9=20.; a10=5.; kon=10;
kpon=0; d1=0.4; d2=0.5; d3=0.42; d4=0.8; d5=0.4;
d6=0.8; d7=0.6; d8=0.4; d9=0.6; d10=0.4; d1a=0; koff=0.05;
kpoff=koff; k1=0.1; k2=0.1; k3=0.1; k4=0.1; k5=0.1; k6=0.1;
k7=0.1; k8=0.1; k9=0.1; k10=0.1; kratio=1; k1a=100;
k9a=kratio*k7;
k5a=kratio*k3;

The following commands and syntax will solve the system of differential equations using the above parameters and initial conditions as specified following the arrow "initialConditions", and will plot all variables. The result will be returned as a list of Mathematica® "interpolating functions" that are assigned to the variable sol. The interpolating functions will contain predicted values of the function for a "timespan" of 500 seconds (e.g., an interpolated table of values):

sol=run [s,
initialConditions→
{K [2,0][0]==0.2,
K [3,0][0]==0.3,
K [1,0] [0]==0.4,
RAFP [0]==0.3,
MEKP [0]==0.2,
MAPKP [0]==0.3,
S [−1, −1, −1] [0]==0.1, RAFK [0]=0.1
},
timeSpan→500,
plotVariables→All]

The following function gives an example of how a single parameter of interest, the integrated total concentration of a particular molecule over some time period, e.g., 100 seconds, can be calculated from the above interpolatingFunctions. First, define the function that is to be evaluated:

integratedOutput [t_, q_]:

$$\int_{ton}^{ton+i} First[Evaluate[K[1,1][time]/.q]d1time$$

Finally, evaluate the function on the Cellerator™ solution:

integratedOutput[100,sol]/.ton→0

The output generated for this exemplary input is 0.827749.

Figure 7:
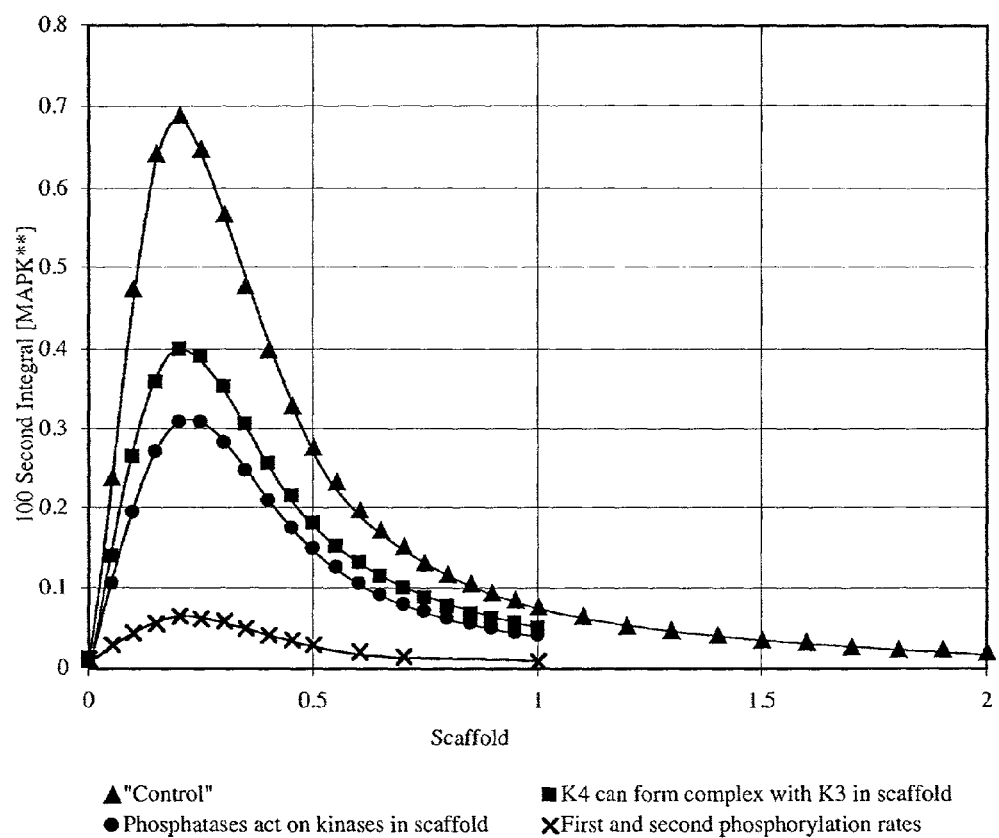
FIG. 7 provides a graph showing the effect of relaxing several assumptions made in the previous report. The time integral of free dually phosphorylated MAPK over first 100 sec. is plotted vs. scaffold concentration. The "control" curve (triangles) reproduces the data with all the assumptions made previously, whereas the other curves represent the results of relaxation of these assumptions such that K4 can form a complex with K3 in a scaffold (squares); phosphatases act on kinases in a scaffold (diamonds), and the first and second phosphorylation rates are equal (X). All data were obtained using the Cellerator™ package and are plotted in Microsoft Excel. Triangles represent resulting values for a control simulation; squares represent values obtained for a simulation performed where K4 can form a complex with K3 in the scaffold; Circles represent resulting values for a simulation performed where phosphatases act on kinases in the scaffold; and X represents values obtained for a simulation performed where the first and second phosphorylation rates are equal.

The use of Cellerator™ using syntax and commands similar to those described above, allowed us to perform systematic sensitivity analyses of the assumptions made in our description of the role of scaffold proteins in MAPK cascade regulation (Levchenko et. al., 2000) using commands and syntax similar to that described above. We previously described dual MAPKK and MAPK phosphorylation within the scaffold to proceed as a single step (processive activation). This is substantially different from a two-step dual phosphorylation sequence occurring in solution. In this distributive activation, the first phosphorylation event is first followed by complete dissociation from the activating kinase and subsequently the second phosphorylation reaction occurs. The assumption of processive phosphorylation in the scaffold has some experimental basis. Mathematically, it is equivalent to assuming that the rate of the second phosphorylation reaction is fast compared to the first reaction. Although this assumption was partially relaxed in our previous report, no systematic study of relaxation of this assumption has been performed. Using the Cellerator™ software to run a method of the present invention, we performed a systematic investigation of the role of increasing or decreasing the rate of the second phosphorylation within the scaffold compared to reactions in solution by using the rates from Table 4, and increased or decreased by a factor of 1000. The results for the case when the two rates are equal are presented in FIG. 7. It is clear that relaxation of this assumption results in a substantial decrease of efficiency of signal propagation.

Similar simulations were performed to investigate the effect of allowing formation of a complex between MAPKKK in the scaffold and MAPKKK-activating kinase, as well as the effect of allowing phosphatases to dephosphorylate scaffold-bound kinases. In all cases the parameter values used in simulation are equal to those used for corresponding reactions in solution (for the full list of parameters see Levchenko et al., 2000). The results are presented in FIG. 7. Again, new assumptions resulted in substantial down-regulation of efficiency of signal propagation. It is of interest that the position of the optimum scaffold concentration (i.e., the concentration at which the maximum signaling is achieved) is insensitive to making these new assumptions. This agrees with the analysis in (Levchenko et. al., 2000), which suggested that the position of the optimum is determined only by the total concentrations of the kinases and their mutual interaction with the scaffold.

The results presented in this Example show that automatic model generation according to the present invention can simplify the transition from an informal, cartoon-based description of a reaction pathway, or a network of pathways, to a system of differential equations. This transition is obtained via a rigorous description of enzymatic kinetics and other biochemical processes and is implemented utilizing symbolic translation. In addition to facilitating the potentially burdensome task of correctly writing out all of the necessary equations, this methodology provides an explicit and flexible way of controlling successive stages of model creation. Furthermore, user intervention is possible both at the stage of conversion of an informal pathway description into a set of chemical reactions and at the later stage of mapping these reactions to the corresponding mathematical forms. This flexibility increases the ability of the user to participate in building and modifying the model at a level limited only by his or her expertise.

We have demonstrated the automatic generation of symbolic differential equations using a generic three-member scaffold, the MAPK cascade mediated signaling system. The implementation of software that performs methods of the present invention, as demonstrated in this Example, called Cellerator™, is capable of generating and solving these 101 differential equations, a task not achieved in the previous detailed study of the effect of scaffolds. Such automated model generation will prove especially useful in describing even more complex biochemical reactions that involve the formation of multi-molecular complexes. Such complexes may exist in numerous states, each requiring a corresponding equation for its dynamical description. Because of the combinatoric expansion of reaction possibilities, correctly writing out all of these equations by hand rapidly becomes impossible.

One of ordinary skill in the art based on the present disclosure, will recognize that methods of the present invention can be used to analyze the role of scaffolds in signal transduction regulation. For example, extended indexing can be used to specify reactions occurring in various sub-cellular compartments. This facilitates the study of the effect of scaffold translocation to the cell membrane observed in gradient sensing and other important regulatory processed. In addition, the algorithm can be developed to allow for scaffold dimerization, an experimentally observed phenomenon.

The computer interface, Cellerator™, which was used in the present Example to perform a method according to the present invention to model events in a linear pathway mediated by sequential covalent modification, can be made more universal to include other canonical forms and variable structure systems. For example, the computer interfaces can be adapted to study the NF-κB and PKA pathways. Consideration of these pathways will necessitate implementation of the elementary reactions describing transcription, translation and protein degradation. In addition, complex formation will be considered as a high level reaction leading to an activation step within the pathway.

EXAMPLE 2

Simulation of a Developmental System

This example provides illustrates the use of the methods of the present invention for automatic model generation of a developmental system. The minimal developmental system can be illustrated using Goldbeter's minimal cascade for mitotic oscillations (Goldbeter, A., *Proc. Natl. Acad. Sci.*

USA, 88:9107-1101 (1991)). It should be noted that any system of differential equations can be used here, so long as there is at least one threshold that will trigger cell division. This particular system was chosen for illustrative purposes because of its elegant simplicity. The differential equations are $$C' = v_i - \frac{v_d X C}{K_d + C} - k_d C \quad (112)$$

$$M' = V_1 \frac{1-M}{K_1 + (1-M)} - V_2 \frac{M}{K_2 + M} \quad (113)$$

$$X' = M V_{m3} \frac{1-X}{K_3 + (1-X)} - V_4 \frac{X}{K_4 + X} \quad (114)$$

where C, M, and X represent Cyclin concentration (C) and the fractions of active CDC2 kinase (M) and cyclin protease (X), respectively, with the additional constraint that $$V_1 = \frac{V_{m1} C}{K_C + C} \quad (115)$$

All other parameters in the equations are constants.

The first differential equation (112) is straightforward; the first and third terms are creation and annihilation of C, $$\{\varnothing \rightleftarrows C, vi, kd\} \quad (116)$$

while the middle term is a hill-function annihilation of C catalyzed by X:

$$\left\{ C \xrightarrow{X} \varnothing, \text{hill}[v\max \to vd, khalf \to kd] \right\} \quad (117)$$

Equations (113) and (114) use implicit mass conservation; for example, the first term in equations 113 is $$\{\text{Comp}[M] \rightarrow M, \text{hill}[v\max \to V1, khalf \to K1]\} \quad (118)$$

and so forth for the remaining reactions. The constraint (115) is enforced utilizing Mathematica® replacement rules. The entire set of reactions is illustrated in FIG. 8.

Figure 10:
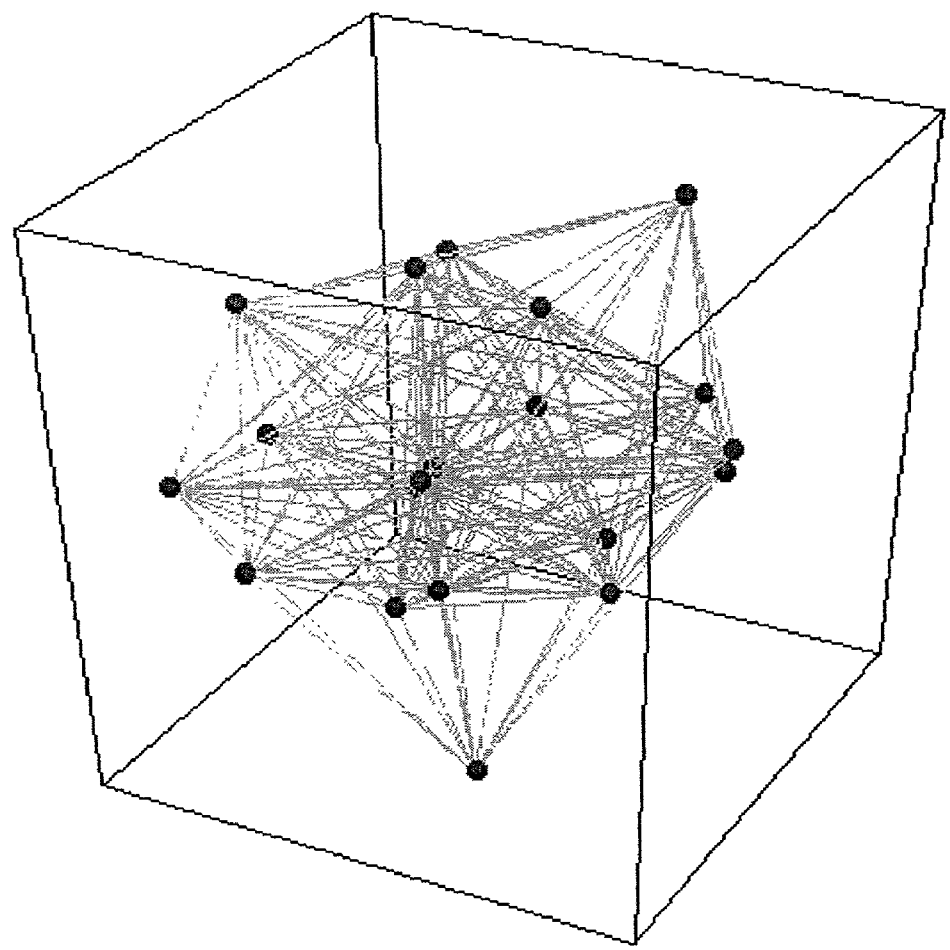
FIG. 10 illustrates an organism-as-graph with 20 cells.
Figure 11:
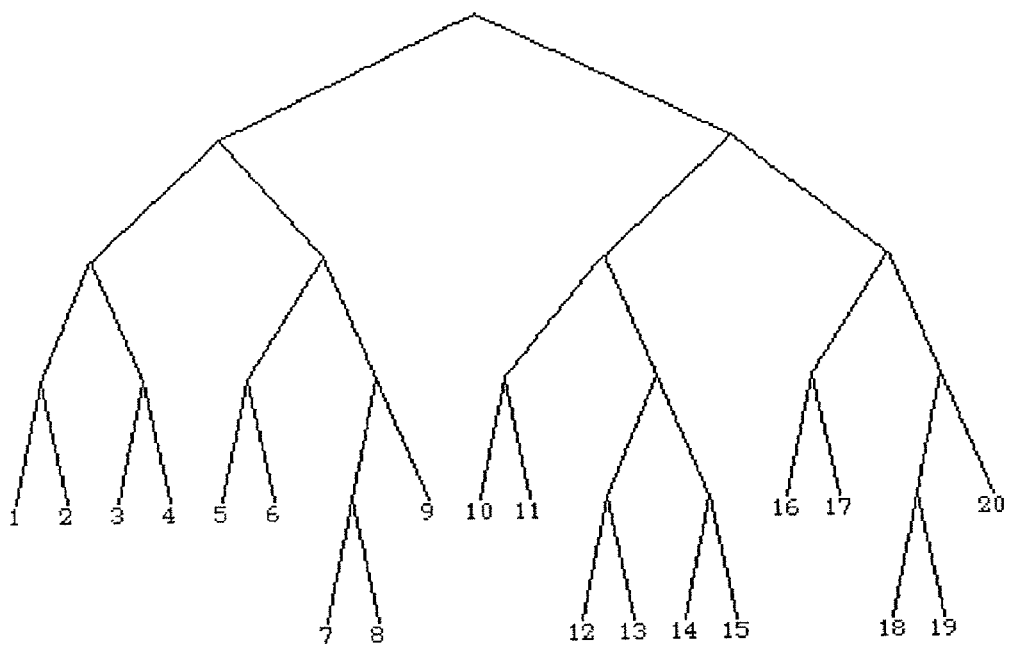
FIG. 11 illustrates a lineage (family tree) of the simulation of FIG. 10.

The Cellerator™ run function will automatically perform a simulation (numerically solve the ODEs using NDSolve) and plot the resulting concentration profiles, as illustrated in FIG. 8. It is not necessary to interpret the reactions first; this is done in FIG. 8 merely for illustrative purposes. To perform a simulation a graphDomain with appropriate initial conditions (cell geometry, initial concentrations, ODEs) for the system of interest is first created. The initial graph domain for a single-celled system is illustrated in FIG. 9; the initial geometry for a multi-cellular system is illustrated in FIG. 4. The second model Domain in FIG. 9 implements the variable-structure threshold described hereinabove, with variables splitflag and tsplit representing $y_1$ and $z_1$ respectively. The system can then be repeatedly integrated using NDSolve, testing the values of the flags after each step. Whenever a threshold is passed, a new node is added to the graph. The concentrations of C, M, and X are randomly split between parent and child cell after each cell division so that the total number of molecules remains fixed before and after cell division. FIG. 10 shows a snapshot of the graph when the organism has grown to twenty cells. (At the point illustrated in FIG. 10 the system had 354 links and 180 ODEs.) Each time a cell divides, a new cell number (equal to N+1 where N is the number of cells in the graph just before cell division) is assigned to the child cell while the parent retains its old cell number (the first cell is number 1). The corresponding node on the lineage tree is replace by a binary subtree tree[parent,child]. The final lineage tree is illustrated in FIG. 11. A different simulation would produce a differently shaped organism because of the nature of the random number assignments.

This Example presents a graph-based methodological paradigm for computational simulations in developmental biology. Multi-cellular systems (organisms) are represented as graphs whose nodes and links represent cells and intercellular interactions, respectively. This approach has a natural hierarchical generalization that makes it very amenable to multi-scale analyses: when more detail is needed, the data stored in a graph node can be expanded into a graph representing the intracellular signal transduction network (STN) of that cell. Nodes on the STN are themselves progressively more detailed signal transduction sub-networks, and so forth, down to a single molecular species, if so desired. Because it would be pointless to try to deterministically simulate every chemical species in every cell at every time such a multi-scale approach becomes essential.

All of the references cited herein are incorporated by reference. Although the invention has been described with reference to the above examples, it will be understood that modifications and variations are encompassed within the spirit and scope of the invention. Accordingly, the invention is limited only by the following claims.

What is claimed is:

1. An automated method for simulating a developmental process of an organism, said method comprising:
   a) receiving initial condition values and process parameters for the developmental process of the organism;
   b) representing the organism or a tissue within the organism by a graph data structure, wherein the graph data structure comprises:
      i) a list of links, each link representing the interaction between two cells;
      ii) a lineage tree recording the family tree of cell birth for the cells represented by the list of links; and
      iii) a list of nodes, each node representing a cell of the cells represented by the list of links, with an embedding describing the location of the cell in Cartesian coordinates and a set of differential equations describing the time evolution of the location of the cell, said differential equations comprising the initial condition values and process parameters, each node comprising a model that comprises a system of differential equations and associated parameters describing the developmental process; and
   c) repeatedly solving the set of differential equations in a series of steps for a defined number of steps, wherein after each step results are generated and compared to a threshold to determine whether the developmental process has reached a trigger point for changing the number of nodes in the list of nodes, thereby simulating the developmental process,
   wherein the developmental process is cell division, and wherein reaching the trigger point adds a new node to the list of nodes.

2. The method of claim 1, wherein the automated method is implemented using a computer algebra program.

3. The method of claim 1, further comprising:
   d) graphing the nodes using the Cartesian coordinates.

4. The method of claim 1, wherein the differential equations further describe a cell cycle pathway checkpoint.

5. The method of claim 1, wherein the differential equations further describe a signal transduction network of the cell.

6. An automated method for simulating a developmental process of an organism, said method comprising:
   a) receiving initial condition values and process parameters for the developmental process of the organism;
   b) representing the organism or a tissue within the organism by a graph data structure, wherein the graph data structure comprises:
      i) a list of links, each link representing the interaction between two cells;
      ii) a lineage tree recording the family tree of cell birth for the cells represented by the list of links; and
      iii) a list of nodes, each node representing a cell of the cells represented by the list of links, with an embedding describing the location of the cell in Cartesian coordinates and a set of differential equations describing the time evolution of the location of the cell, said differential equations comprising the initial condition values and process parameters, each node comprising a model that comprises a system of differential equations and associated parameters describing the developmental process; and
   c) repeatedly solving the set of differential equations in a series of steps for a defined number of steps, wherein after each step results are generated and compared to a threshold to determine whether the developmental process has reached a trigger point for changing the number of nodes in the list of nodes, thereby simulating the developmental process,
   wherein the developmental process is cell death, and wherein reaching the trigger point deletes a node from the list of nodes.

7. The method of claim 6, wherein the automated method is implemented using a computer algebra program.

8. The method of claim 6, further comprising:
   d) graphing the nodes using the Cartesian coordinates.

9. The method of claim 6, wherein the differential equations further describe a cell cycle pathway checkpoint.

10. The method of claim 6, wherein the differential equations further describe a signal transduction network of the cell.

* * * * *